(12) United States Patent
Munoz et al.

(10) Patent No.: US 10,888,156 B2
(45) Date of Patent: Jan. 12, 2021

(54) APPLICATOR TOOL CLEANER AND DRYER

(71) Applicant: KML Lifestyles, LLC, Penngrove, CA (US)

(72) Inventors: Keiri E. Munoz, Penngrove, CA (US); Armen Gardabad Ohanian, Granada Hills, CA (US); Herach Ayvazian, Burbank, CA (US)

(73) Assignee: KML LIFESTYLE LLC, Westlake Village, CA (US)

( * ) Notice: Subject to any disclaimer, the term of this patent is extended or adjusted under 35 U.S.C. 154(b) by 293 days.

(21) Appl. No.: 15/337,951

(22) Filed: Oct. 28, 2016

(65) Prior Publication Data
US 2017/0119145 A1 May 4, 2017

Related U.S. Application Data

(60) Provisional application No. 62/249,757, filed on Nov. 2, 2015.

(51) Int. Cl.
*A46B 17/06* (2006.01)
*F26B 9/00* (2006.01)
(Continued)

(52) U.S. Cl.
CPC .............. *A46B 17/065* (2013.01); *F26B 3/04* (2013.01); *F26B 9/003* (2013.01); *F26B 25/22* (2013.01); *A61L 2/10* (2013.01); *A61L 2202/17* (2013.01)

(58) Field of Classification Search
None
See application file for complete search history.

(56) References Cited

U.S. PATENT DOCUMENTS

| 586,404 A | 7/1897 | Tyler et al. |
| 2,822,814 A | 2/1958 | Torkelson |
| (Continued) | | |

OTHER PUBLICATIONS https://www.lilumia.com/product/lilumia-2/ (3 pgs.).
(Continued)

*Primary Examiner* — Mikhail Kornakov
*Assistant Examiner* — Natasha N Campbell
(74) *Attorney, Agent, or Firm* — DLA Piper LLP (US)

(57) ABSTRACT

Apparatuses and methods of cleaning and drying applicator tools, such as brushes, cosmetic applicators, or cosmetic tools, are disclosed. An applicator tool cleaning apparatus according to various embodiments includes an applicator tool holder configured to hold multiple applicators of various sizes with the applicator heads facing down. The applicator tool cleaning apparatus further comprises a cleaning chamber that can dispense liquid to saturate the applicator heads and contact the applicator heads with a textured surface to dislodge collected materials on the applicator heads. Additionally, the applicator tool cleaning apparatus may comprise a drying chamber where drying mechanisms blow air or dissipate heat at the applicator heads until dried. The applicator tool holder may be moved vertically between the cleaning chamber and the drying chamber via a motor and drive mechanism of the applicator tool cleaning apparatus. Alternatively, in some embodiments, the applicator tool holder may be flipped such that the applicator heads are facing upwards and aligned with the drying mechanisms.

8 Claims, 18 Drawing Sheets

(51) Int. Cl.
*F26B 25/22* (2006.01)
*F26B 3/04* (2006.01)
*A61L 2/10* (2006.01)

(56) References Cited

U.S. PATENT DOCUMENTS

| | | | |
|---|---|---|---|
| 2,853,085 A | 9/1958 | Torkelson | |
| 2,994,330 A | 8/1961 | Catlin et al. | |
| D191,469 S | 10/1961 | Lewis | |
| 3,129,451 A | 4/1964 | Colaianni | |
| 3,225,377 A | 12/1965 | Winter | |
| 3,805,318 A | 4/1974 | Marquette | |
| 3,982,296 A | 9/1976 | Russo | |
| 4,403,364 A * | 9/1983 | Schroeder | A46B 17/06 15/38 |
| D276,705 S | 12/1984 | Oliveri | |
| D318,240 S | 7/1991 | Pang et al. | |
| 5,107,877 A | 4/1992 | Chipman | |
| 5,652,991 A | 8/1997 | Kashani | |
| 5,701,626 A | 12/1997 | Zara et al. | |
| 5,881,876 A | 3/1999 | Nonomura et al. | |
| D421,216 S | 2/2000 | Abrams | |
| D492,822 S | 7/2004 | Wang | |
| 6,935,515 B1 | 8/2005 | Sookoo | |
| D513,341 S | 12/2005 | Ullmann | |
| D513,948 S | 1/2006 | Martin | |
| D516,257 S | 2/2006 | Brackett et al. | |
| 7,086,112 B2 | 8/2006 | Smith et al. | |
| 7,140,061 B2 | 11/2006 | Baker et al. | |
| 7,458,944 B2 | 12/2008 | Liste et al. | |
| 7,594,291 B1 | 9/2009 | Carmen | |
| 7,871,651 B2 | 1/2011 | Sinichko | |
| D669,232 S | 10/2012 | Chung | |
| 8,485,001 B2 | 7/2013 | Mette | |
| D703,415 S | 4/2014 | Khan | |
| 8,763,966 B2 | 7/2014 | Supnik | |
| D737,136 S | 8/2015 | Lam | |
| D737,540 S | 8/2015 | Borella | |
| D747,621 S | 1/2016 | Amerson | |
| 9,277,805 B2 | 3/2016 | Baker et al. | |
| 9,380,860 B1 * | 7/2016 | Taylor | A46B 17/06 |
| D779,137 S | 2/2017 | Taylor | |
| 2003/0046798 A1 | 3/2003 | Valles Camps | |
| 2004/0181887 A1 | 9/2004 | Smith et al. | |
| 2007/0023064 A1 * | 2/2007 | Gilbert | A61L 2/025 134/1 |
| 2007/0056130 A1 | 3/2007 | Baker et al. | |
| 2011/0232681 A1 | 9/2011 | Hatfield | |
| 2012/0199168 A1 | 8/2012 | Campbell | |
| 2013/0000062 A1 | 1/2013 | Brackett et al. | |
| 2013/0117977 A1 | 5/2013 | Kennedy | |
| 2014/0000052 A1 | 1/2014 | Filho et al. | |
| 2014/0096801 A1 * | 4/2014 | McCormick | B08B 11/02 134/115 R |
| 2014/0189969 A1 | 7/2014 | Baker et al. | |
| 2015/0060373 A1 | 3/2015 | Byeon | |

OTHER PUBLICATIONS https://www.lilumia.com/product/lilumia-2-dubai/ (3 pgs.).
https://www.lilumia.com/product/lilumia-2-new-york/ (3 pgs.).
https://www.lilumia.com/product/lilumia-2-tokyo/ (3 pgs.).
https://www.lilumia.com/product/lilumia-makeup-brush-cleanser/ (2 pgs.).
https://www.lilumia.com/product/power-supply/ (1 pgs.).
https://www.lilumia.com/product/cleaning-disk/ (2 pgs.).
https://beautyforbrekkie.com/2016/04/stylpro-makeup-brush-cleaner/ (8 pgs.).

* cited by examiner

FIG. 8(A)
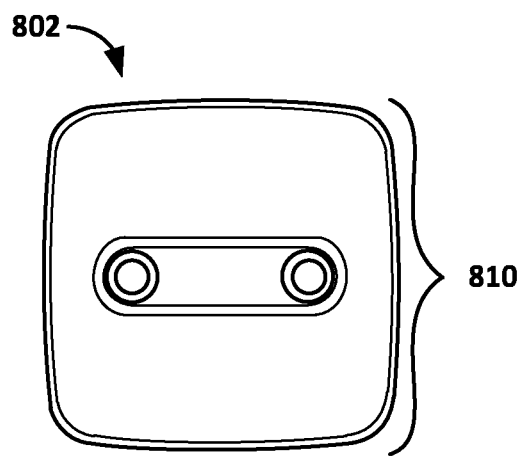
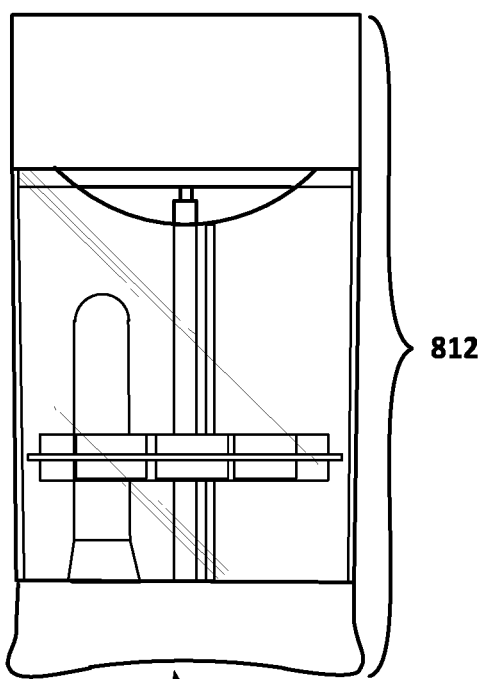
FIG. 8(B)
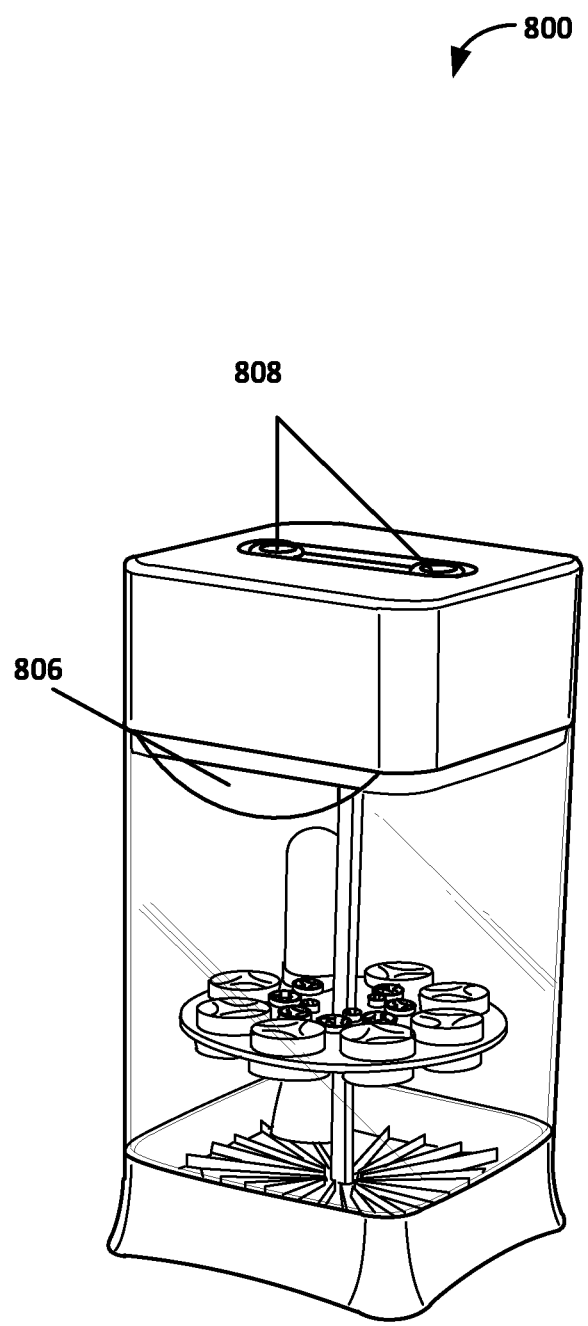
FIG. 8(C)

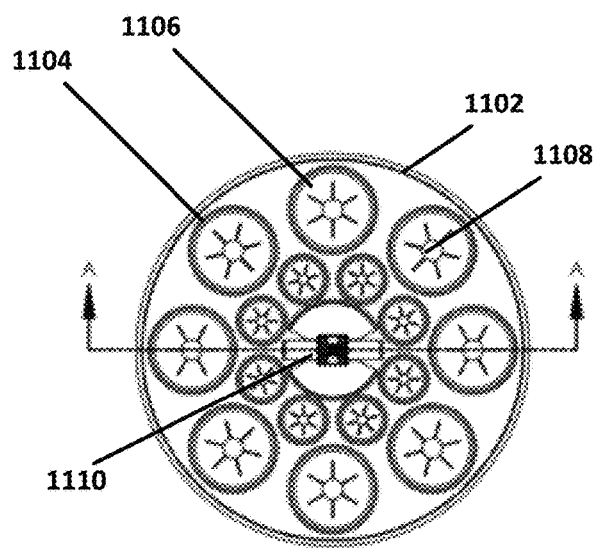
FIG. 11(A)
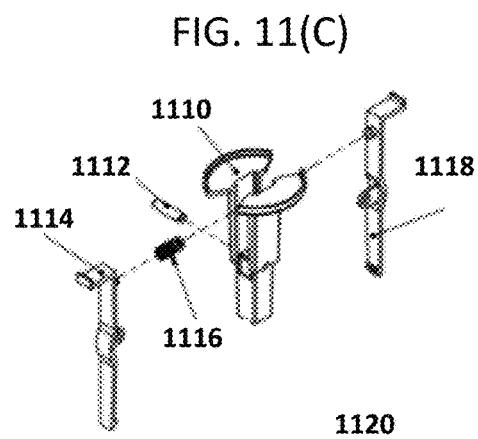
FIG. 11(C)
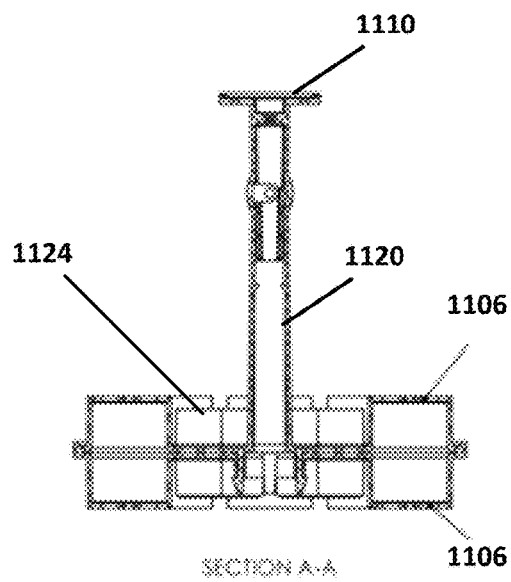
FIG. 11(B)
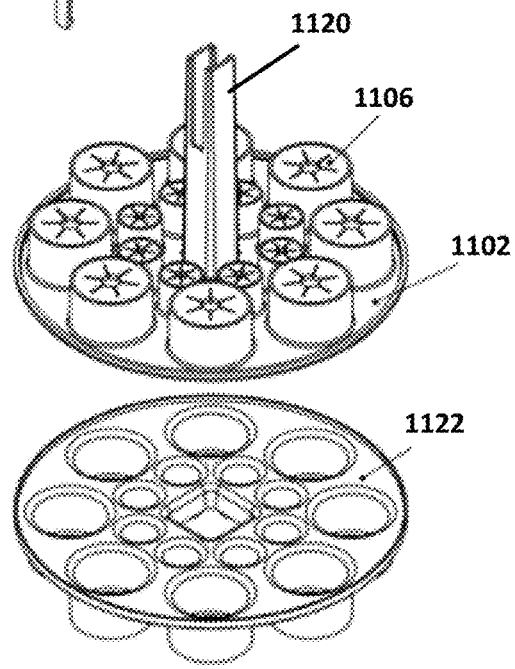

APPLICATOR TOOL CLEANER AND DRYER

CROSS-REFERENCE TO RELATED APPLICATIONS

The present application claims priority to Provisional U.S. Application No. 62/249,757, entitled "MAKEUP BRUSH CLEANER AND DRYER," filed Nov. 2, 2015, which is incorporated herein by reference for all purposes.

BACKGROUND

Brushes, such as those used to apply cosmetics, often collect materials and accumulate residue from previous cosmetic applications that prevent the brushes from adequately applying makeup uniformly or blending makeup evenly. Other cosmetic applicator tools, such as eyelash curlers, eyebrow combs, or sponges, also need routine cleanings so that their utility is not diminished by accumulated residue. In addition, failure to clean the applicator tools may raise health concerns. For example, accumulation of old cosmetics (e.g., makeup powders, liquid makeup), skin cells, and oil residue on applicator tools can result in the formation of bacteria on the applicator heads that cause acne if the applicator tools are left unwashed before future applications. There are various rudimentary tools, such as rubber gloves or pads, that can be used to manually clean and dry these brushes, but they require a significant amount of time and effort, and do not adequately remove all cosmetic residues or other accumulated material, like dust or dander. The inability to remove all material can reduce the effectiveness of the applicator tools, or negatively impact the intended cosmetic effect or appearance of makeup applied using those applicator tools, and in some instances may even provide a potential health risk depending upon the type of material accumulating over time. Further, generally separate applicator tools are used for different types of applications or different makeup. Therefore only one applicator tool can be cleaned at a time so that other tools can be used in the meantime, as opposed to cleaning all the tools at once. If any type of liquid or cleaner is used, the applicator tool will also have to be manually dried over long periods of time, usually between 24 to 48 hours, during which the applicator tool will have to sit unused until the applicator tool is sufficiently dry for its intended purpose.

BRIEF DESCRIPTION OF THE DRAWINGS

Various embodiments in accordance with the present disclosure will be described with reference to the drawings, in which:

FIGS. 8(A)-(C) illustrate views of a third example tool holder component in accordance with one embodiment.

FIGS. 11(A)-(C) illustrate views of a fourth tool holder component in accordance with one embodiment.

DETAILED DESCRIPTION

Systems and methods in accordance with various embodiments of the present disclosure may overcome one or more of the aforementioned and other deficiencies experienced in conventional approaches to cleaning and maintaining applicator tools and other instruments. In particular, various embodiments provide an apparatus for cleaning and/or drying multiple applicator tools concurrently.

Figure 1A:
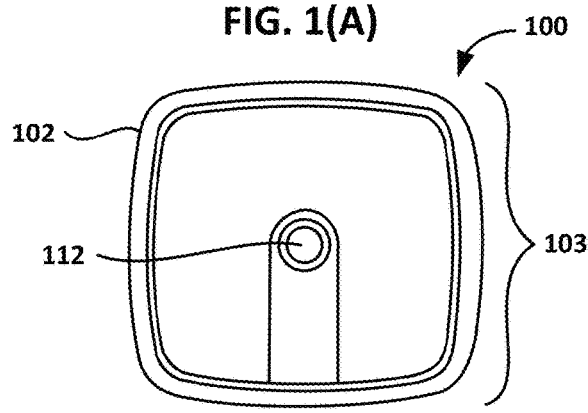
FIGS. 1(A)-(C) illustrate views of a first example cleaning device in accordance with one embodiment.
Figure 1B:
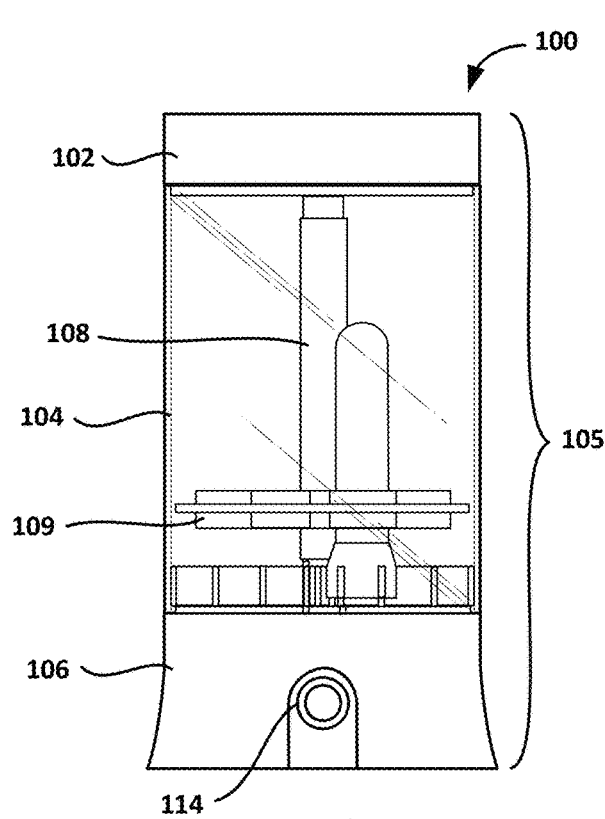
Figure 1C:
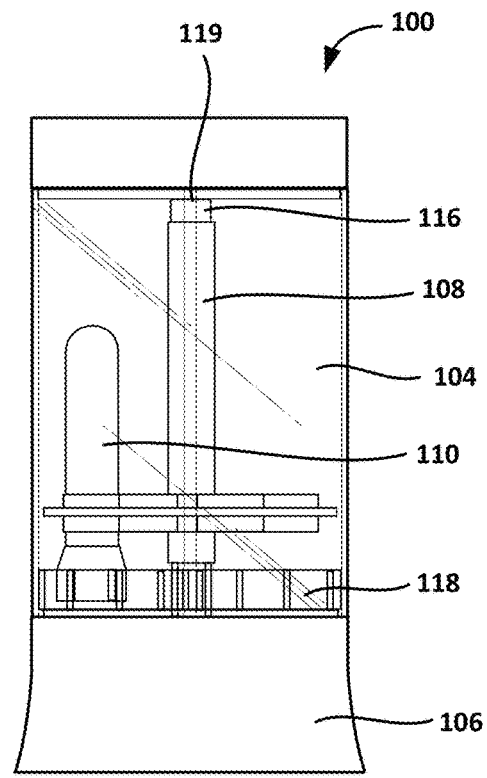

FIGS. 1(A)-(C) illustrate multiple views of an example of one such device 100. This example shows a housing formed of three main parts, a top portion 102, a middle portion 104, and a bottom portion 106, as shown in FIG. 1(B). Each of the parts can be made out of an appropriate, sturdy, and lightweight material such as a plastic or polymer, although aluminum, glass, metal, and other materials can be used as well in various embodiments. Each portion can also be available in different colors, designs, or styles in some embodiments. In this example, as shown in FIG. 1(A), the top portion 102 may have a width 103, and the width 103 and shape of the top portion 102 may be varied based on the number of applicator tools that the device 100 can hold. For example, the shape of the top portion 102 may be a square, a rounded square, a circle, or triangle. Applicator tools can include, among other things, cosmetic brushes for powders such as kabuki brushes, foundation brushes, eye shadow brushes, eye brow brushes, bronzer brushes, or blush brushes. Other brushes for liquid or gel makeup may also be cleaned or dried by the applicator tools cleaning and drying device, for example eye liner brushes, lip brushes, or concealer brushes. Other applicator tools can include, among other things, eyelash or eyebrow combs, mascara wands, or sponge-tipped applicators. Brushes for body paint or other uses may also be cleaned or dried by the applicator tools cleaning and drying device. Depending on the shape of the top portion 102 and the width 103, the arrangement of applicator tools may be varied to optimize the number of applicator tools that can be cleaned or dried at once.

As shown in FIG. 1(B), in this example the device 100 also has a height 105 that may be varied to any suitable height to accommodate a variety of applicator tools and applicator tool lengths. In this example the middle portion 104 is transparent, or at least translucent, such that brushes or other objects placed within the cleaning device are visible from outside the device. The applicator tool holder can hold a number of applicator tools and sizes, and can include a central shaft 108 and a tray 109. In some examples the middle portion 104 may be fixed to the bottom portion 106, such as by using a glue, screw, or other connection mechanism, while in other embodiments the middle portion may be removably attached. The top portion 102 in this example can be removable from the middle portion 104, with a portion of the top portion capable of being received by the middle portion 104 in order to create a substantially water-tight seal between the top and middle portions. In some embodiments the top portion can be attached to the housing by a hinge or similar mechanism, among other options.

As shown in FIG. 1(C), the middle portion 104 in this example includes an interior region shaped to receive a washing member, such as an applicator tool holder having a central shaft 108 and a tray 109. The applicator tool holder can be received by a drive mechanism 116, such as a rotor or axle, which can be received by, or attached to a central shaft 108 of the applicator tool holder having a tray 109. The drive mechanism 116 can be connected to a motor contained within the bottom portion 106 in order to rotate, oscillate, vibrate, or otherwise provide a source of motion to the applicator tool holder. It should be understood that in some embodiments the applicator tool holder may remain stationary or be rigidly attached to an inside of the housing and that a cleaning member or other mechanism may move instead of (or in addition to) the applicator tool holder. Other options can be utilized as well. When the device is fully assembled and not performing a cleaning or drying cycle, the device can also be used as an applicator tool storage unit.

In this example the top portion 102 and the bottom portion 106 can each include, among other things, a source of power, such as a battery compartment, a rechargeable battery, unrechargeable battery, a power cord, etc. In this example the bottom portion 106 can include a power cord or power port, for example, capable of receiving power, which can be provided to a battery inside the top portion 102 through one or more leads 119 running along the drive shaft 116 or along an interior/exterior of the middle portion 104, among other options. As shown in FIG. 1(A), a first on/off button 112 is illustrated on the top portion 102 in order to activate a drying mechanism (such as a heater and/or fan), and in FIG. 1(B), a second on/off button 114 is illustrated on the bottom portion 106 in order to activate the rotating mechanism or other cleaning mechanism, although a switch or other activation mechanism can be used in place of either button as well, or a single button may be used on either portion. The drying mechanism (such as a heater and/or fan), including any electronics, may be contained within the top portion 102. Further, there may be other activation mechanisms used, such as separate mechanisms for initiating a washing cycle, a drying cycle, insert of water, draining of water, setting a time or temperature, etc. The housing is also illustrated to include, among other things, at least one light, such as an LED, integrated within the lower second on/off button 114 to indicate an active status of the device. The light may have multiple colors, or there might be multiple lights, to convey different states of the device. There may also be a display, speaker, or other mechanism for conveying state or other information to a user.

As shown in FIG. 1(C), a plurality of ridges 118, protrusions, or other cleaning elements can be included, among other things, in the interior of the middle portion 104 when the device is assembled, where those elements can be part of the middle portion 104 or the bottom portion 106. The cleaning elements 118 can be designed such that when an applicator tool, such as a brush 110, is placed in the applicator tool holder 108, the hairs, fur, bristles, or other application portion of the applicator tool will be adjacent the cleaning elements during the execution of a cleaning cycle. During motion of the applicator tool tray 109 around the applicator tool central shaft 108, the application portion or applicator head will be gently moved across the cleaning elements in order to cause material buildup to be dislodged from the application portion. In some embodiments, after the cleaning cycle is completed, the applicator tool holder, both the tray 109 and the central shaft 108 may be removed and flipped (this configuration is not shown), such that the applicator head is facing the top portion 102. A fan or other drying mechanism may be turned on in the top portion 102 to dry the application portion of the applicator tools. The top portion 102 and middle portion 104 may include vents, aerated perforations, or other openings to allow for air circulation to dry and/or store the applicator tools.

Figure 2:
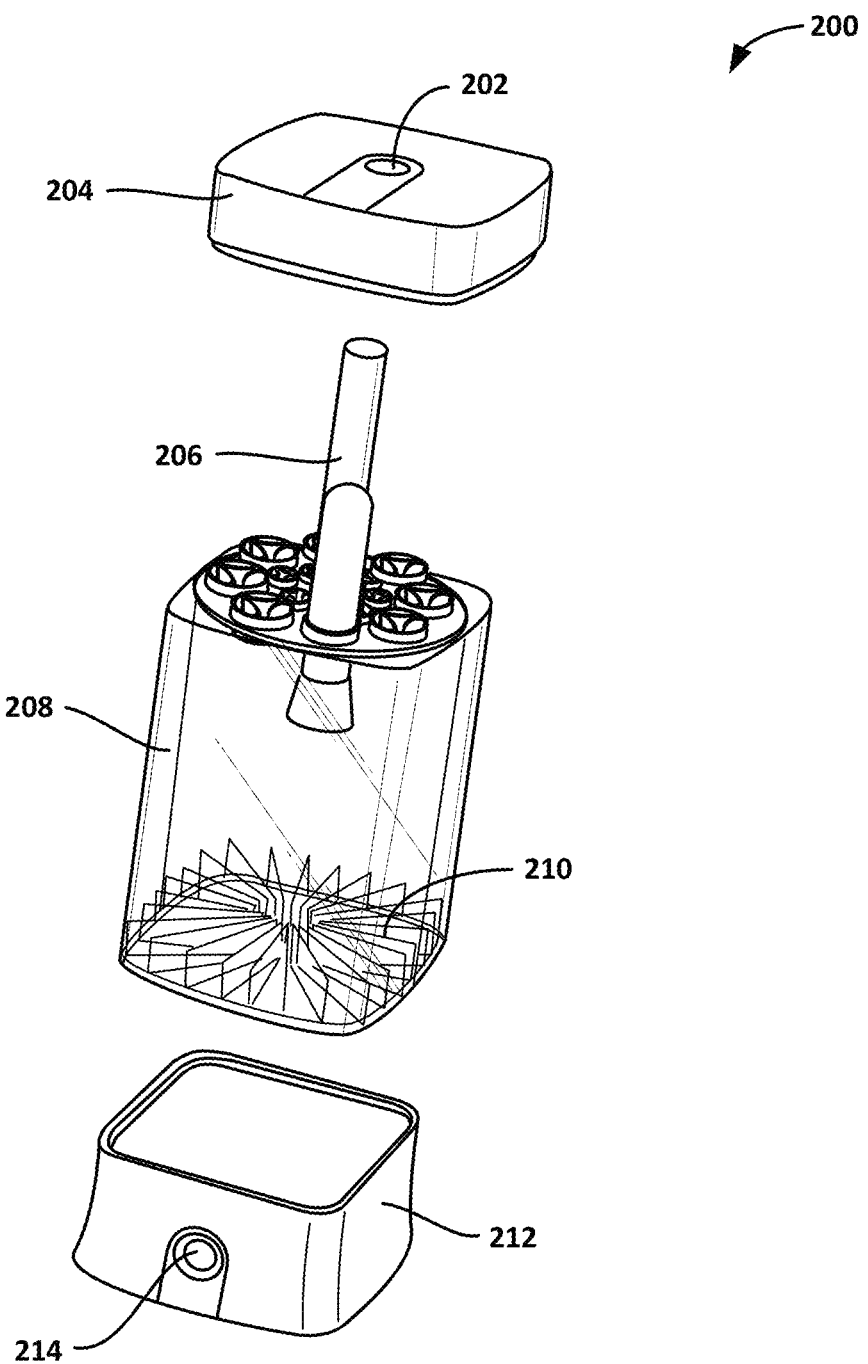
FIG. 2 illustrates an exploded view of the first example cleaning device in accordance with one embodiment.

FIG. 2 illustrates an exploded view 200 of the first example cleaning device. As illustrated in this view, it can be seen that the top 204, middle 208, and bottom 212 portions are separately formed pieces, with the cleaning members 210 (or "debris removal ribs" in this example) molded or otherwise formed into an interior of the middle portion 208. As illustrated, the top button 202 in this example functions as an on/off button for a fan contained within the top portion that is configured to direct air across the brushes held by the applicator tool holder. Although the applicator tool holder 206 is illustrated in an orientation for cleaning the brushes, it should be understood that the orientation can be switched such that the bristles of the brushes are adjacent the top portion in order to more directly receive the air from the fan mechanism. The top portion 204, or fan housing, can be formed of an appropriate material such as acrylonitrile butadiene styrene (ABS). The applicator tool holder 206 can be made of the same or a similar material, such as ABS, a thermoplastic elastomer (TPE), polypropylene (PP), or other materials. The applicator tool holder 206 shown is capable of holding up to twenty applicator tools, although other numbers and variations of brushes (or other instruments) can be held as well in other embodiments. The middle portion 208, or "tank" portion, can be designed to receive and hold a water solution, and can be made of a material such as a polycarbonate (PC). In this example the tank 208 is removable in order to enable easy addition and removal of the water solution. The cleaning members 210 as illustrated are ribs molded into the tank portion 208. As with the top portion 204, the bottom portion or base 212, can be formed of a material such as ABS, or other materials, and can include, among other things, an on/off button 214 to activate the motor and cause the drive shaft to impart motion unto the applicator tool holder 206, whereby the brushes are moved across the cleaning ribs 210 as discussed previously. Also as mentioned, a rechargeable battery can be contained within the base portion and/or top portion, which can be charged using an appropriate charging mechanism such as a power cord or other appropriate power source. Alternatively, the base portion may be configured to receive external power, for example, through a charging cord into a power source or outlet.

Figure 3A:
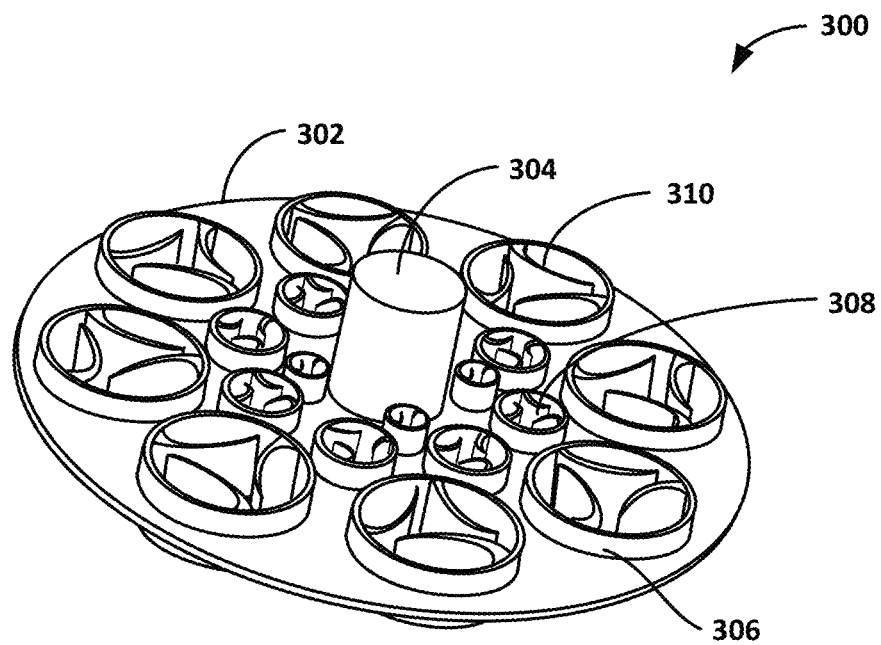
FIGS. 3(A)-(B) illustrate views of a first example tool holder component in accordance with one embodiment.
Figure 3B:
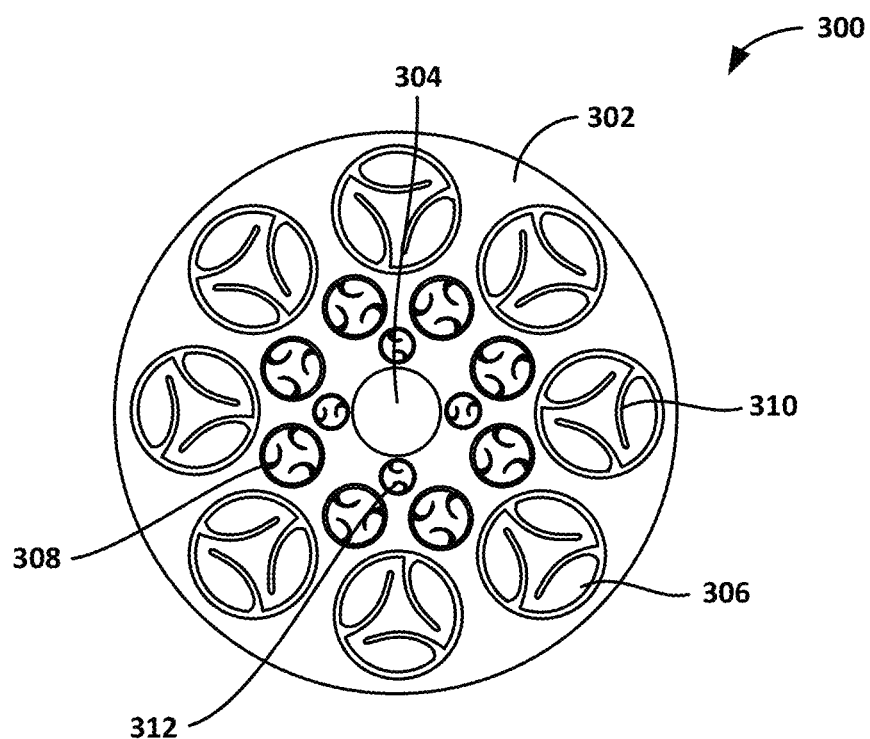

FIG. 3(A) illustrates a perspective view of an example applicator tool holder 300 that can be used in accordance with various embodiments, and FIG. 3(B) illustrates a top view of the example applicator tool holder 300 that can be used in accordance with various embodiments. As illustrated, there can be a number of applicator tool holder openings 306, 308, and 312, which can be of the same size or different sizes or designs in order to hold similar or different types of applicator tools and/or instruments, such as, for example, brushes. For example, as illustrated in FIG. 3(B), a large size applicator tool holder opening 306 may be suitable for brushes with thick handles, like foundation or kabuki brushes, or any other cosmetic applicator tools used for wide area coverage. The medium size applicator tool holder opening 308 may be suitable for blush or bronzer brushes, or other cosmetic applicator brushes for medium area coverage. The small size applicator tool holder opening 312 may be suitable for eye shadow, eye liner, or concealer brushes, or any other cosmetic applicator brush for precise coverage. The applicator tool holder openings 306, 308, 312 may be arranged on a tray 302 with a column or axle 304 orthogonal at the center of the tray 302. The column 304 can be used for rotating the tray 302 or for attaching a handle to remove the tray 302 holding the applicator tools. The holder can be of any appropriate material as discussed, such as ABS, PP, or TPE, or other materials. In this example each opening includes a set of three interior ribs 310. The ribs 310 can be molded into the holder, and can be designed to flex (i.e., act like a spring) in order to receive and hold applicator tools of various sizes in the respective openings. Thus, the material selected could be flexible enough to be able to allow the ribs 310 to flex to receive, for example, brushes of different thicknesses, or applicator tool portions with different thicknesses, while being rigid enough to hold the applicator tools in place. In some embodiments the ribs 310 for an opening 306, 308, 312 can be part of a separate piece, such as a rubber or plastic piece shaped to fit in the opening and provide the appropriate ribs or other holding members. Such an approach enables different sizes or types of ribs 310 to be utilized as may be able to hold different types of applicator tools, as well as to replace any ribs that may lose rigidity after repeated use. The ribs 310, in this example, each are curved to help provide flexibility and ease of brush placement, although other designs and numbers of ribs can be used as well within the scope of the various embodiments. The openings and ribs may also, in some embodiments, be replaceable or swappable such that the applicator tool holder may be customizable. For example, the holder 300 may be customized to hold, clean, and dry all large brushes or all small brushes. Further, although the holder 300 is shown to be used at a fixed height in certain examples, it should be understood that the height might be adjustable or moveable. Alternatively, different holders may be available in order to hold applicator tools of different heights, sizes, or design.

In one example approach, a user would place the desired number of brushes in the applicator tool holder, fill the tank with the appropriate solution, then place the applicator tool holder with the brushes in the tank and attach the top member. The user would then push the bottom button to cause the device to run through a cleaning cycle, whereby the brushes are oscillated or otherwise moved to cause the bristles to move across the cleaning mechanism to remove debris. An oscillating motion may be used, such as may cause the applicator tool holder to oscillate back and forth by 180 degrees, rotate a full 360 degrees, or perform another motion. Various oscillation strengths and speeds can be used as well as discussed elsewhere herein. A light in the bottom button can indicate the status of the cycle. When completed, the user can remove the top portion and dump the water solution from the tank. The user can optionally flip the applicator tool holder and insert the applicator tool holder into the base portion to cause the bristles to be closer to the top portion. The user can then reattach the top portion and press the top button in order to cause the dryer (such as a heater and fan mechanism) to dry the brushes for a determined period of time, although in other embodiments the time might be controlled by the user or a moisture sensor, among other options. When the drying is complete, the user can remove the brushes from the applicator tool holder and use them for their intended purpose(s). Alternatively, the brushes can remain in the applicator tool holder and the device may be used as an applicator tool storage unit.

Figure 4:
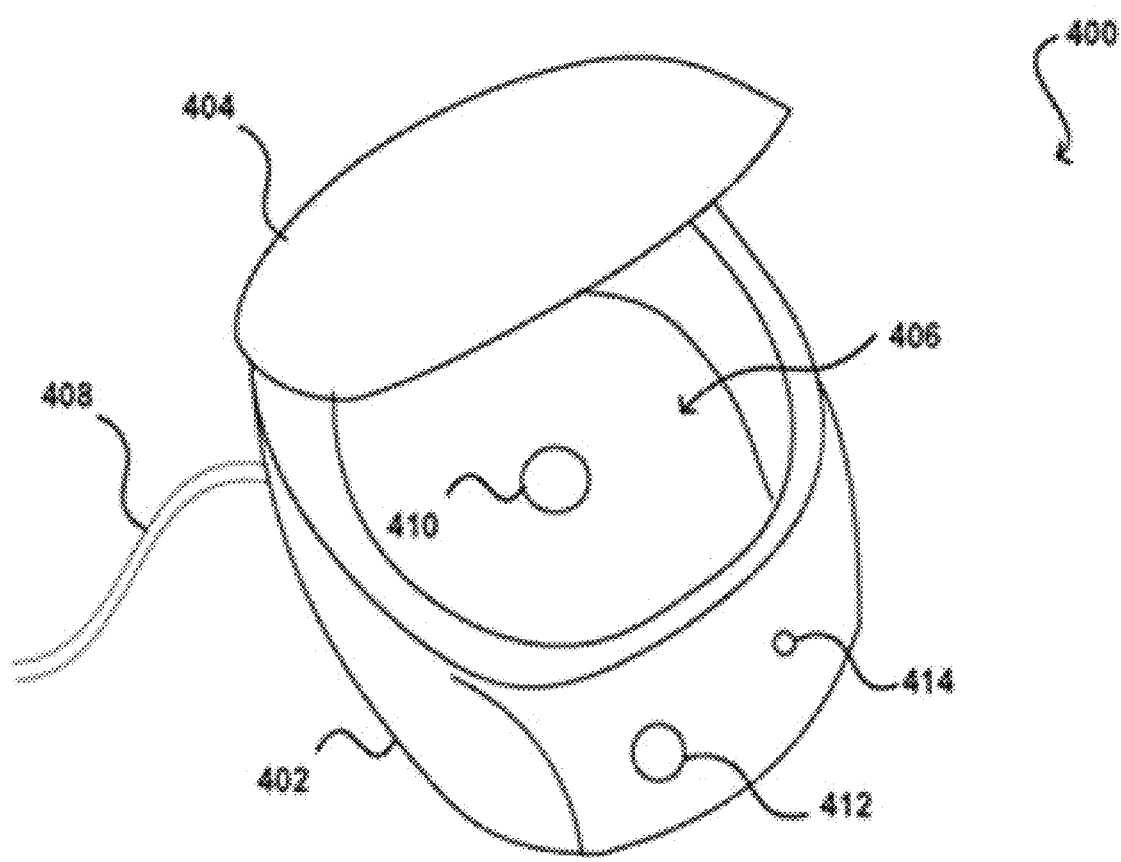
FIG. 4 illustrates a perspective view of a second example cleaning device in accordance with one embodiment.

FIG. 4 illustrates another example cleaning device 400 that can be used in accordance with various embodiments. As should be apparent, there can be many designs and arrangements used within the scope of the various embodiments to accomplish the functionality discussed and suggested herein. This example shows a housing formed of three main parts, a top portion 404, a middle portion 405, and a bottom portion 402. Each of the parts can be made out of an appropriate, sturdy, and lightweight material such as a plastic or polymer, although aluminum, metal, and other materials can be used as well in various embodiments. In this example the middle portion 405 can be transparent, or at least translucent, such that applicator tools or other objects placed within the cleaning device are visible from outside the device. In some examples the middle portion 405 may be fixed to the bottom portion 402, such as by using a glue, screw, or other connection mechanism, while in other embodiments the middle portion may be removably attached. The housing has a top portion 404, which can be attached to the housing by a hinge or similar mechanism, or can be removable from the housing. The top or lid portion 404 in this example opens to expose an interior region 406 of the middle portion 405. The interior region can be designed to be water tight in at least some embodiments, and can be shaped to receive a washing member (not shown). The housing can include, among other things, a drive mechanism 410, such as a shaft or other member capable of connecting with the washing member in order to rotate, oscillate, vibrate, or otherwise provide a source of motion to the washing member. It should be understood that in some embodiments the washing member may remain stationary or be rigidly attached to an inside of the housing and that an applicator tool holder or other mechanism may move instead of (or in addition to) the washing member. Other options can be utilized as well. The cleaning device can also include, among other things, a source of power, such as a battery compartment, a rechargeable battery, a power cord 408, or other power source. An on/off button 412 is illustrated, although a switch or other activation mechanism can be used as well. Further, there may be other activation mechanisms used, such as separate mechanisms for initiating a cleaning cycle, a heating cycle, a drying cycle, insert of water, draining of water, setting a time or temperature, etc. The housing is also illustrated to include, among other things, at least one light 414, such as an LED, to indicate an active status of the device. The light may have multiple colors, or there might be multiple lights, to convey different states of the device. There may also be a display, speaker, or other mechanism for conveying state or other information to a user. The device may be powered by an internal power source, such as a rechargeable battery or other battery, or may be powered by an external power source, such as through a cable with a plug to an outlet.

Figure 5:
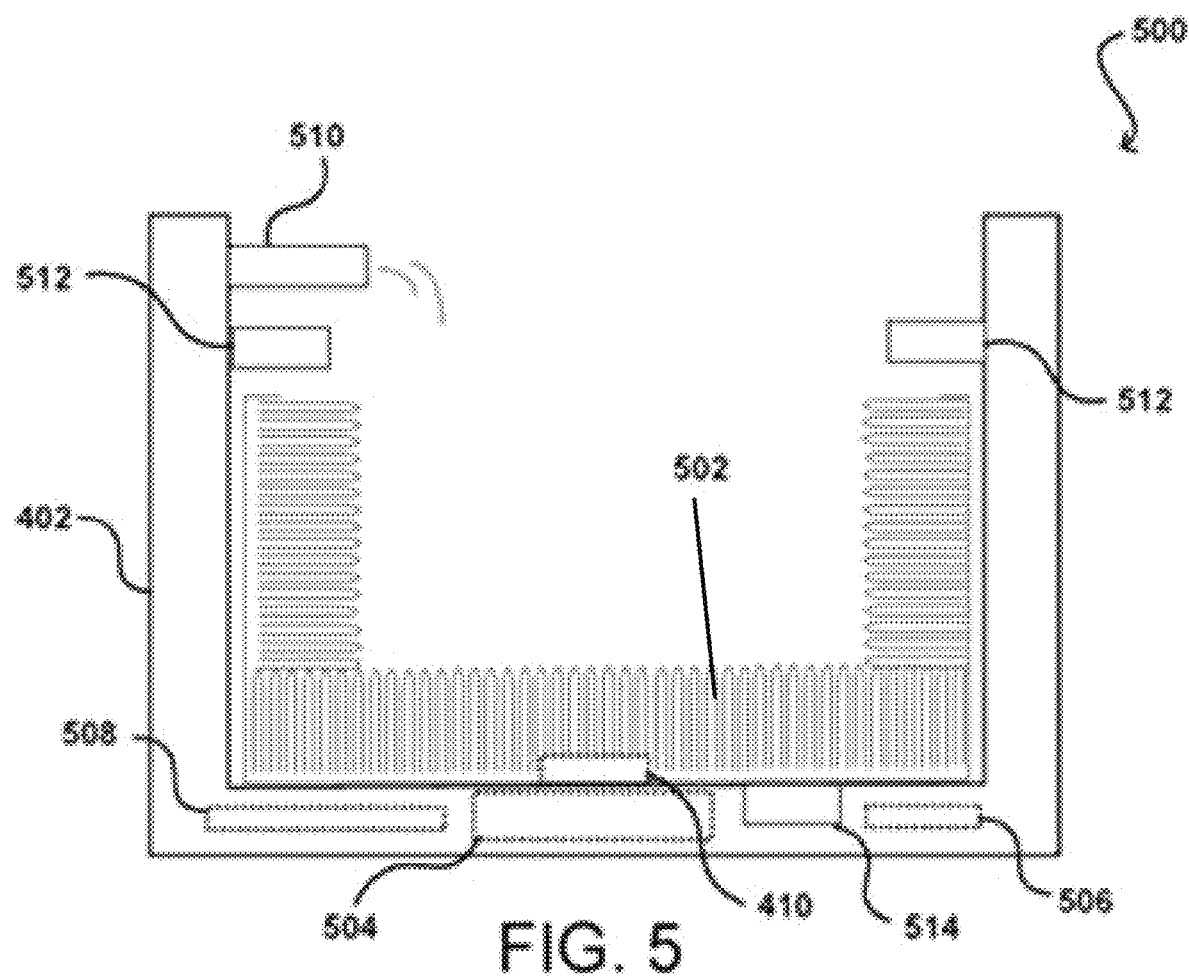
FIG. 5 illustrates a cross-section view of the second example cleaning device in accordance with one embodiment.

FIG. 5 illustrates a cross-section view of an example washing device 500 in accordance with one embodiment. Reference numbers may be carried over for simplicity of explanation, but such usage should not be interpreted as a limitation on the scope of the various embodiments unless specifically stated. In this view, a cross-section of the housing 402 is displayed, with a motor 504 shown to be configured to drive the drive mechanism 410. The motor can be any appropriate motor, such as a brush motor, brushless motor, variable frequency drive, induction motor, synchronous motor, and the like. The motor can work with internal circuitry 506 (i.e., controller circuit board) to receive start and stop signals, drive commands, and the like. The view also includes a washing member 502 capable of being driven by the drive mechanism 410. The washing member here is a rotatable member, although other motions or materials can be used as well in other embodiments, including the applicator tool holder moving while the washing member is stationary or fixed. The member also includes a plurality of cleaning members, such as may be made of a rubber, plastic, polymer, silicone, or other (at least somewhat) flexible material. The cleaning members can be of the same, or a different, material than the rotatable member. The material may also be rubber, plastic, or other materials, but in a shape that allows for the breakdown of particles built up in the brushes. When driven by the drive mechanism 410, the cleaning brushes of the washing member can engage the bristles of brushes placed within the interior of the device, causing material and/or contaminants to be freed from the bristles or other portions of the brushes. As mentioned, the device can also include some internal power source 508, such as a rechargeable battery or other battery, or may be powered by an external power source including through a cable with a plug.

In at least some embodiments, liquid can be used to help clean the applicator tools. Accordingly, at least one liquid inlet 510 can be included in at least some embodiments. The liquid can come from any appropriate source, such as a reservoir of the device or an external hose. In other embodiments a user may manually pour the liquid into the interior opening of the device, among other options. In some embodiments the liquid will be a cleaning liquid, either premixed or mixed in the device. If mixed in the device, the mixture can come from an additive that is either a liquid or a dissolvable material added to the internal opening, or tank, either manually by a user or from a tablet, solution, reservoir, or other source. In other embodiments the liquid may be added to the applicator tool themselves before being placed in the tank. For devices utilizing liquid, at least one drain 514 or other outlet can be used to drain the liquid, although in other embodiments a user may manually drain the liquid by tilting the device or tank itself. In this view, the device also includes one or more drying mechanisms 512, which can include, among other things, hot air dryers, cool air dryers, fans, or other drying mechanisms. In some embodiments the drying mechanism activates automatically after one or more wash cycles, although in other embodiments the drying mechanism must be activated manually by a user, among other options. In other embodiments there may be no drying step at all, or the drying might have to be manually selected or initiated by a user, among other options.

Figure 6:
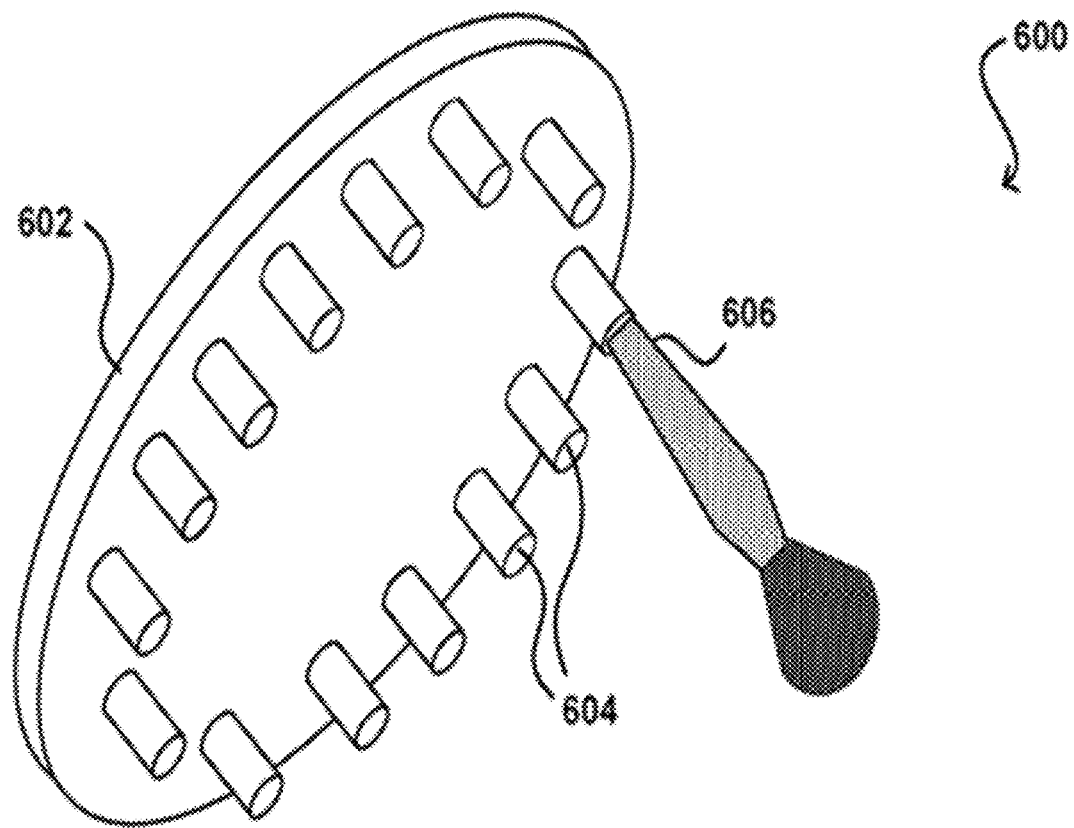
FIG. 6 illustrates a perspective view of a second tool holder component in accordance with one embodiment.

FIG. 6 illustrates a cross-section view of an example applicator tool holder 600 that can be utilized in accordance with various embodiments. The holder includes a bulk member 602 with a variety of applicator tool receptacles 604, although various other arrangements and holding mechanisms can be used as well. In this example the bulk member or tray is a disc-shaped piece of a material such as plastic, rubber, aluminum, or a polymer, although other shapes and materials can be used as well. The applicator tool receptacles 604 can all be similarly shaped, or can be shaped to hold different types or sizes of brushes 606, as well as to be able to hold other types of applicator tools or instruments. Although a blush brush is shown, it should be understood that this is just one example of the type of instrument that can be held and cleaned using such a device. Other brushes, for example, such as bronzer brushes or eye shadow brushes, can be cleaned as well, among other applicators, tools, and instruments. For example, in some embodiments, the device may be configured to clean other applicator tools other than brushes or tools without bristles, like those with sponge-tipped ends or plastic/rubber tips. In some embodiments a user can add or remove receptacles, adjust placement, change the types of receptacles utilized, etc.

Figure 7:
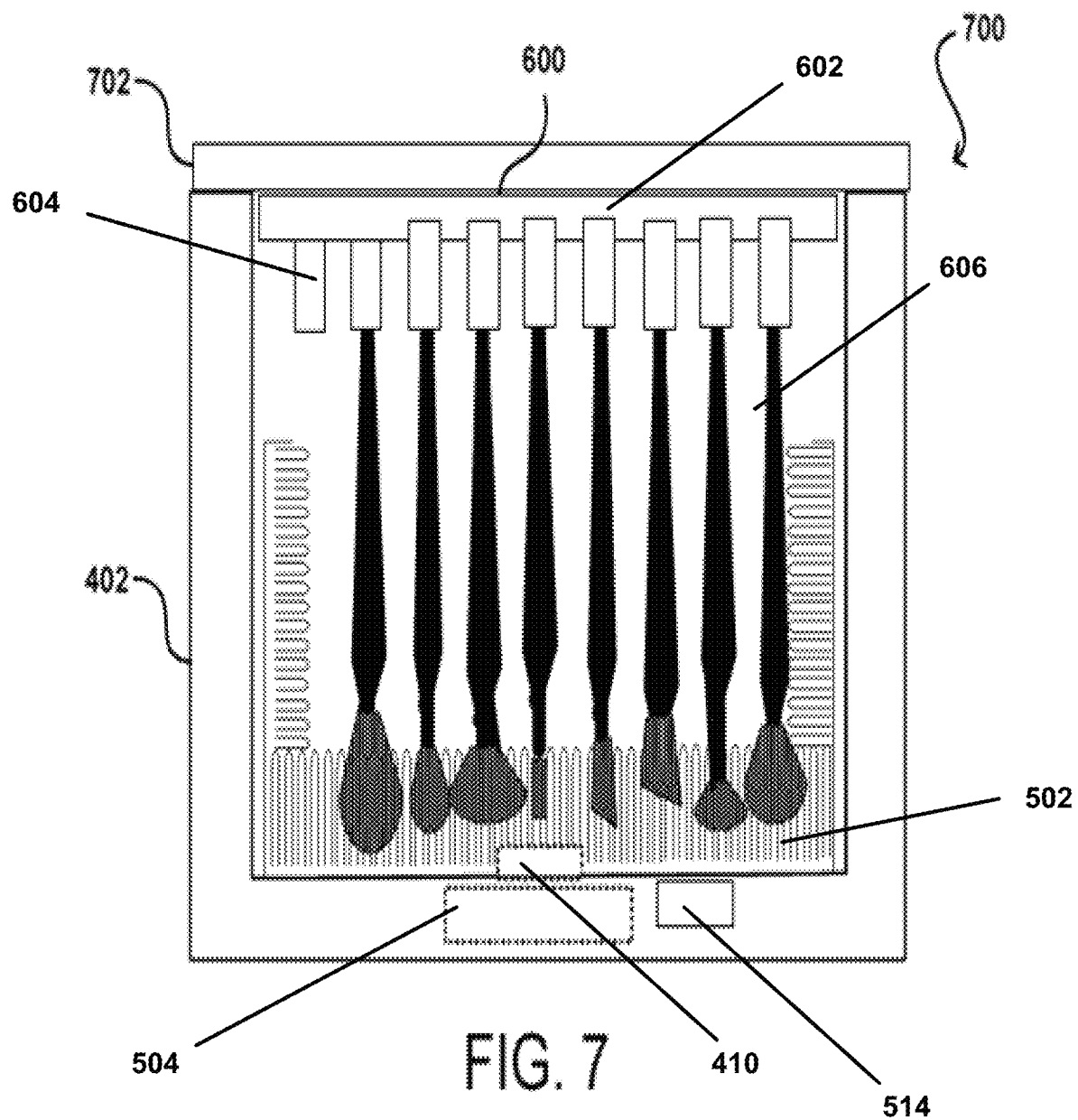
FIG. 7 illustrates a cross-section view of the second example cleaning device in accordance with one embodiment.

FIG. 7 illustrates a cross-section view of one embodiment of the applicator tool holder 600 with brushes in the tank of the housing 402, with the lid 702 closed and the device ready to operate. As illustrated, when positioned in the tank the applicator tool holder 600 positions the makeup brushes 606 so that the cleaning members of the washing member 502 make contact with the brushes. Upon movement of the washing member 502 and/or the brushes 606 via the tray 602, the cleaning members of the washing member 502 can move back and forth between the bristles in order to help remove or dislodge debris or material from the brushes 606. In some embodiments the entire tank 402 will rotate, either with or in addition to the washing member 502. The tank 402 may be rotated or oscillated via a drive mechanism 410 driven by a motor 504. Alternatively or additionally, the applicator tool holder 602 and/or cleaning member 502 may be oscillated, rotated, or moved in a manner to aid in cleaning the applicator tools. The motor 504 may be powered by an internal power source, such as a rechargeable battery or other battery, or may be powered by an external power source including, among other external power sources, through a cable with a plug. The tank 402 can be filled with liquid to clean the brushes 606. For example, the liquid can be a cleaning liquid (e.g., detergent) or a mixture of cleaning liquid and rinsing liquid (e.g., water). After the cleaning liquid mixture saturates the brushes 606 and the brushes have been cleaned by contacting the brushes with the washing member 502, the cleaning liquid is drained through drain 514. The tank 402 can then be filled with a rinsing liquid, such as water, to rinse off any remaining cleaning liquid mixture on the brushes, and the rinsing liquid may be drained through the drain 514. In other embodiments, the tank may be manually removed and the liquid may be poured out. Alternatively, the brushes 606 may be cleaned only with water as the cleaning liquid or a leave-in cleaning liquid that does not need rinsing, thus eliminating another rinsing process after the cleaning process.

FIGS. 8(A)-(C) illustrate a third example of a cleaning device 800 in accordance with various embodiments. In this example, FIG. 8(A) illustrates a top view of the top portion 802 including the battery (or other power source as mentioned herein) and motor(s) for the device, which can drive the oscillation of the applicator tool holding element and include the fan or other drying elements. The width 810 may be any dimension appropriate for accommodating the number of desired applicator tools of varying sizes. As an example, the width 810 of the top portion 802 may be 6.375 inches. FIG. 8(B) illustrates a side view of the cleaning device 800, and the bottom portion 804 in this example is primarily a base portion with little other functionality in this embodiment. The top portion 802 contains two buttons 808 with illumination capability (including different colors for different functions or different cycles within a function), one of which may be used for cleaning (or operating the drive motor for cleaning) and the other of which can be used for drying or other functions, such as to activate a fan and/or heater contained within the top portion. The height 812 may be any dimension appropriate for accommodating applicator tools of different lengths or sizes. As an example, the height 812 of the cleaning device 800 may be 12 inches. As illustrated in the perspective view of the cleaning device 800 in FIG. 8(C), the tank can have a shaped region that creates an air circulation vent 806 when the device is fully assembled, which can help with the cleaning and/or drying processes as well as to allow for circulation if used as an applicator tool storage unit. The vent 806 can also function as a hand insert to help with removal of the top portion and prevent dropping of the tank when filling or draining liquid, among other advantages.

Figure 9:
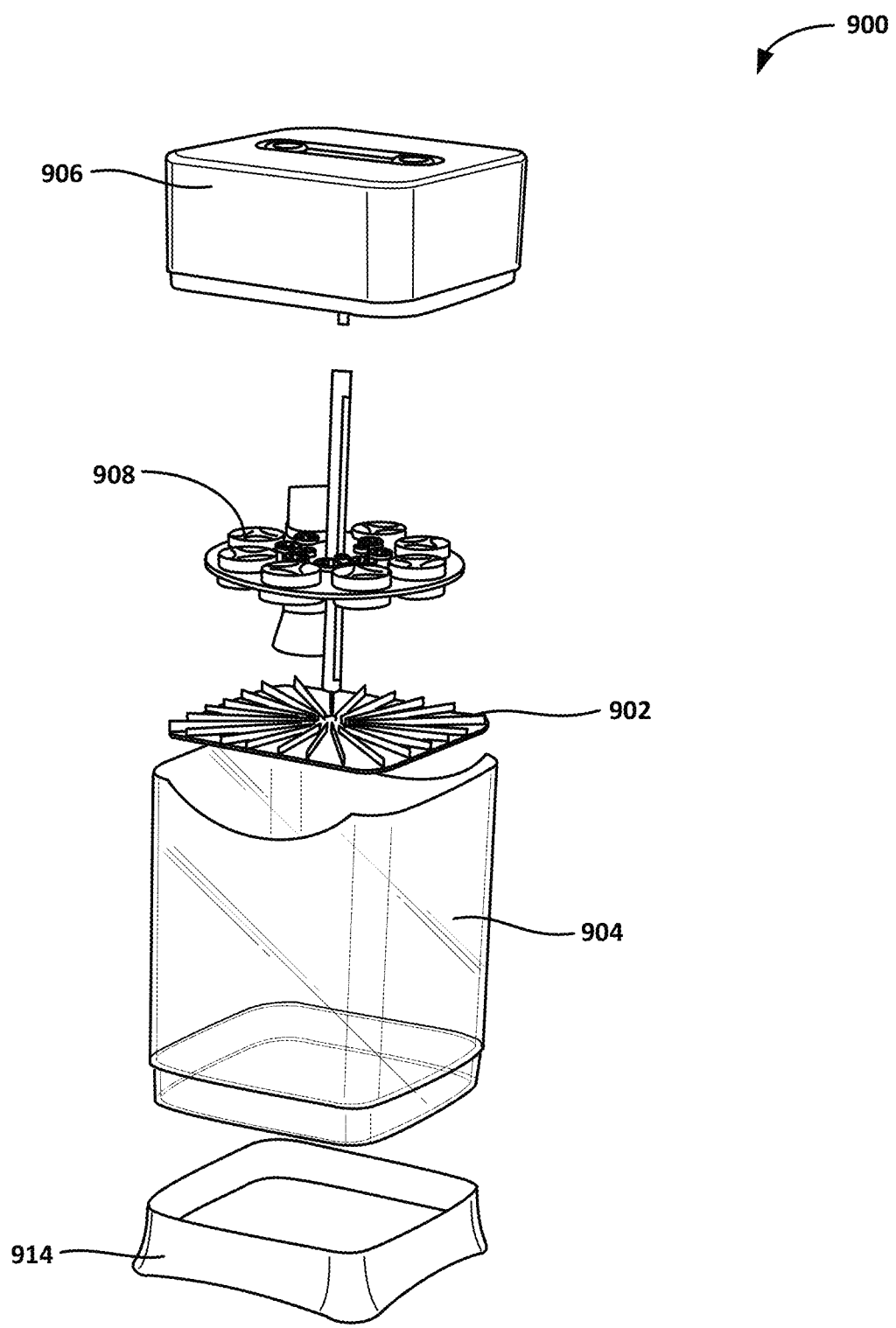
FIG. 9 illustrates an exploded view of the third example tool holder component in accordance with one embodiment.

FIG. 9 illustrates an exploded view 900 of the third example device. As illustrated, in this embodiment the ribs or bristles used to hold the applicator tools for cleaning or drying are part of a removable piece 902, which can be placed in the interior of the tank 904, or middle portion. The middle portion tank 904 can be designed to receive and hold a water solution, and can be constructed of a material such as a polycarbonate (PC), or other materials. In this example the tank 904 is removable in order to enable easy addition and removal of the water solution, or enable cleaning of the tank. Although labeled as made of rubber, it should be understood that the bristles 902 can be made of other materials such as plastics or polymers as mentioned elsewhere herein. The removable piece 902 can also have a central recessed region (or other region) for receiving an end of the applicator tool holding element. As illustrated, the tank portion 904 can be shaped to be received into an opening in the base or bottom portion, although in some embodiments the tank may be glued or otherwise affixed to the base portion 914. The top portion 906 may be housing for electronics, a fan, or a heater, among other things, and can be formed of an appropriate material such as acrylonitrile butadiene styrene (ABS), or other materials. The applicator tool holder 908 can be made of the same or a similar material, such as ABS, a thermoplastic elastomer (TPE), polypropylene (PP), or other materials. The applicator tool holder 908 shown is capable of holding up to twenty multi-sized brushes, although other numbers and variations of applicator tools (or other instruments) can be held as well in other embodiments. The bottom portion 914 serves as a base for the cleaning device 900 and can be constructed of the same or a similar material as the top portion 906, for example ABS, or other appropriate material.

Figure 10:
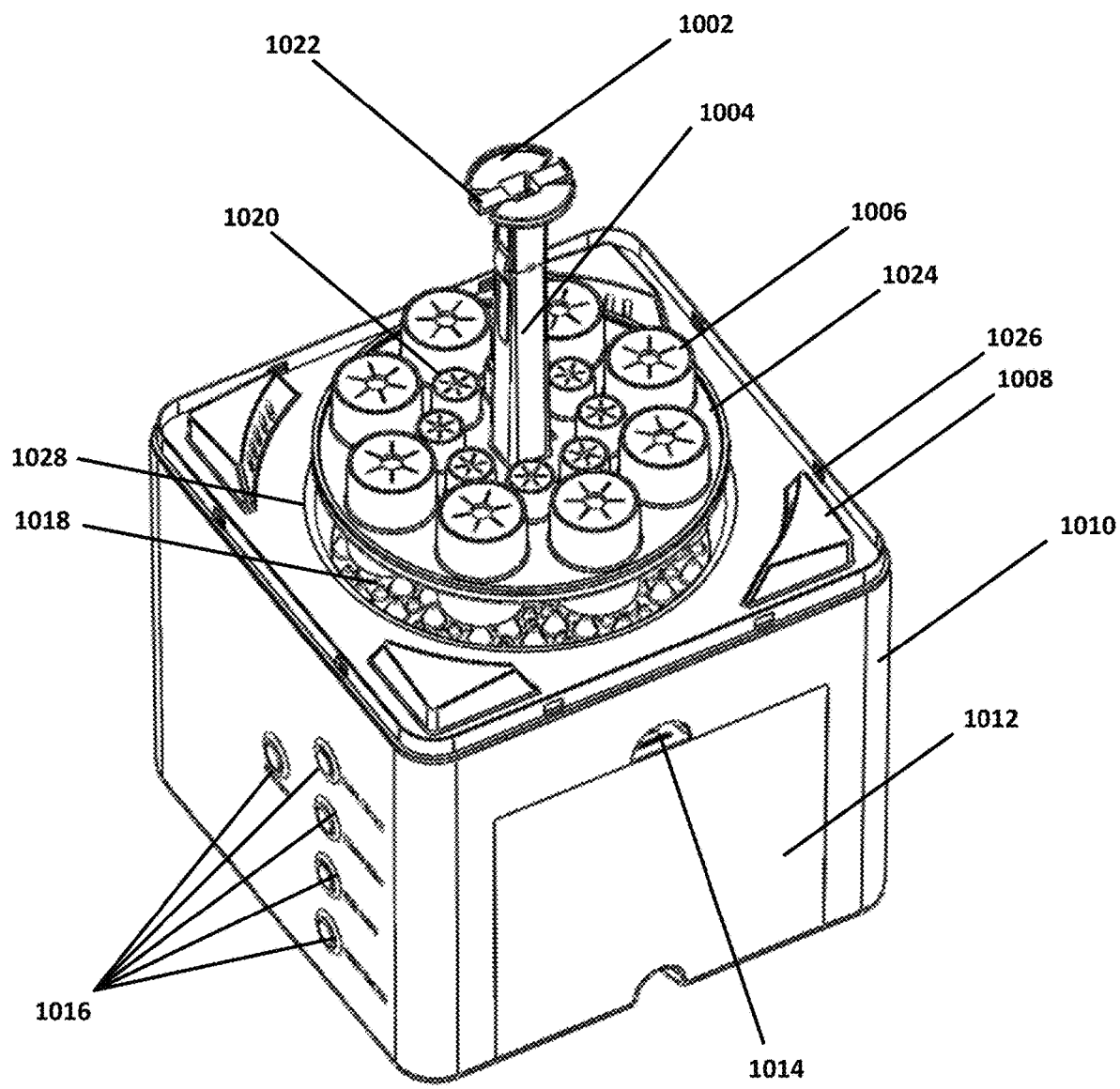
FIG. 10 illustrates a perspective view of a fourth example cleaning device in accordance with one embodiment.

FIG. 10 illustrates a perspective view of a fourth example applicator tool cleaning device 1000 that can be utilized in accordance to various embodiments. In this example, an applicator tool holder includes a tray 1024 with applicator tool receptacles that are overmolded cups 1006 and 1020. The overmolded cups 1006 can have flexible ribs made of rubber or other flexible material to allow, for example, a brush to be inserted and held gently in place by the wand and ferrule of the brush or other applicator tool. To accommodate various sizes of applicator tools, there can be larger sized overmolded cups 1006 and smaller sized overmolded cups 1020. The overmolded cups 1006 and 1020 protrude and extend from the surface of the tray 1024 in the applicator tool holder to create a secure hold on the wands and ferrules of the brushes. This is to maintain the applicator heads of the applicator tools during cleaning, for example, reducing damage to the bristled ends from the brushes shifting and potentially touching or getting tangled each other. Further, to enable a user to move and transport the applicator tool holder, the applicator tool holder may have a handle 1002 with a grip portion. The handle 1002 may be attachable to a shaft 1004 on the tray 1024 by one or more clamp arms 1022 interlocking into grooves on the shaft 1004. The grooves on the shaft 1004 are located a distance from a tip of the shaft. The clamp arms 1022 may be pinched together to release and uncouple the clamp arms tips from the grooves in the shaft 1004. Otherwise, as shown, when the clamp arms 1022 are not pinched together, the clamp arm tips are interlocked with the shaft 1004 such that the handle 1002 may be used to move the applicator tool holder. The shaft 1004 can also be fitted around a column (not shown) to enable the tray 1024 to move vertically in a lower position or an upper position. The cleaning device 1000 further includes a cleaning chamber 1010, and the column may be operatively coupled to a motor and drive mechanism within the cleaning chamber 1010 to enable the applicator tool tray 1024 to be rotated or moved vertically up and down.

In this example, when the applicator tool tray 1024 is in the lower position, the applicator tool tray 1024 is contained with a washing bowl 1028 of the cleaning chamber 1010. Within the washing bowl 1028, at the bottom, a cleaning mat 1018 with protrusions serves to aid in cleaning the applicator tools in the applicator tool holder. The mat 1018 may be removable for easy cleaning and disinfecting. Alternatively, the bottom of the washing bowl 1028 may be textured similarly to the mat 1018. In this example, the cleaning members or protrusions in the mat 1018 may serve to help clean the bristled ends of the brushes when the applicator tool tray 1024 is rotated. Alternatively, the washing bowl 1028 or the mat 1018 may be oscillated to clean the bristles. In some embodiments, the washing bowl 1028 may have inlets (not shown) to dispense liquid into the washing bowl. The liquid can be a cleaning liquid and/or a rinsing liquid. The protrusions in the mat 1018 and the movement of the applicator tool tray 1024, washing bowl 1018, and/or the mat 1018, can help lather the cleaning liquid and also dislodge materials (e.g., dust, cosmetic residue, skin cells, dander, oils) accumulated on the application portions of the applicator tools. Cleaning liquid and/or rinsing liquid can then be drained from the washing bowl 1018. The cleaning chamber 1010 can include, among other things, a tank 1012 that collects the drained liquid. The tank 1012 can be removable to dispose of the collected waste liquid using grip openings 1014. After the cleaning process is complete (i.e., liquid is drained from washing bowl 1028), the drying process can begin. The cleaning chamber 1010 can include various drying mechanisms, such as fans to blow air or heated air into a drying chamber (not shown) above the cleaning chamber to dry the applicator tools. To dry the applicator tools, the applicator tool tray 1024 may be lifted into an upper position within the drying chamber (not shown) such that the application portions of the applicator tools are at the same level as fan outlets 1008. For example, the fans within the cleaning chamber 1010 may blow and direct air through outlets 1008 into the drying chamber to the bristled ends of the brushes to dry them.

Further, in this example, the cleaning device 1000 may include, among other things, an interface 1016 with the user. The interface 1016 can be a combination of buttons for the user to control various processes, such as initiating or stopping the cleaning process, and initiating or stopping the drying process. Additionally or alternatively, the interface 1016 can include, among other things, indicators, lights, or buttons which indicate to the user when a cleaning or drying process is in progress, or when the cleaning or drying process is complete. Indicators can include, among other things, at least one light, such as an LED, integrated within a button to indicate an active status of the device. The light may have multiple colors, or there might be multiple lights, to convey different states of the device. There may also be a display, speaker, or other mechanism for conveying state or other information to a user. In some embodiments, the drying chamber or cleaning chamber 1010 may have various sensors to determine when the cleaning process and/or the drying process is complete. For example, the cleaning process may be timed to saturate the application portions of the applicator tools in the cleaning liquid for a set period of time and then to rinse the applicator tools in rinsing liquid for another period of time. The drying process may also be timed and set to a predetermined period of time estimated to suitably dry the wet brushes. In some embodiments, there can be other sensors, such as a temperature sensor or a moisture sensor to determine whether the applicator tools are dry enough and suitable for use. All of these settings may be configurable in the interface 1016, for example, the interface may allow the user to select the type of cleaning process (e.g., with detergent or rinse with water only), and/or the type of drying process (e.g., by timer, moisture detection, or temperature). The interface 1016 may be a lighted button or a light, such as an LED, to indicate an active status of the device. The light may have multiple colors, or there might be multiple lights, to convey different states of the device. There may also be a display, speaker, or other mechanism for conveying state or other information to the user.

FIGS. 11(A)-(C) illustrates various views of an example applicator tool holder for the fourth example of the cleaning device. FIG. 11(C) shows an exploded view of the applicator tool holder, FIG. 11(A) shows a top view of the applicator tool holder, and FIG. 11(B) shows a cross-section view of the applicator tool holder. In this example and as described in FIG. 10, an applicator tool holder includes a tray 1102 with a number of applicator tool receptacles. In this example, the applicator tool receptacles are overmolded cups 1106 formed to extend around openings 1104 on the surface of the tray 1102. The overmolded cups 1106 may be of various sizes to accommodate different types or sizes of applicator tools, as shown by a smaller overmolded cup 1124 in FIG. 11(B). The overmolded cups 1106 can have flexible ribs made of rubber or other flexible material to securely hold the wand of an applicator tool inserted through an opening 1108. In some embodiments there is a second tray 1122 with openings and overmolded cups that mirror the tray 1102. In this example, the overmolded cups 1106 of the first tray 1102 and the overmolded cups of the second tray 1122 couple together to gently and firmly hold the applicator tool in place when they are being cleaned to avoid applicator heads or bristles from getting tangled with each other. In some embodiments, the overmolded rubber cups 1106 and 1124 may be dispersed on the surface of the tray 1102 with various spacing. For example, the overmolded rubber cups 1106 may be spaced about 40 mm or 1.5 in apart. The smaller overmolded cups 1124 may be spaced with a different distance. In some embodiments the overmolded cups can be part of a separate piece, such as a rubber or plastic piece shaped to fit in the opening and provide appropriate ribs or other holding members. Such an approach enables different sizes or types of holding members to be utilized as may be able to hold different types of applicator tools, as well as to replace any overmolded cups or holding members that may lose rigidity after repeated use. The openings and overmolded cups 1106 and 1124 may also, in some embodiments, be replaceable or swappable such that the applicator tool holder may be customizable or rearranged. For example, the tray 1102 may be customized to hold, clean, and dry all large brushes or all small brushes.

For moving and transporting the applicator tool holder, the applicator tool holder may have a handle 1110 with a grip portion. The handle 1110 may be attachable to a shaft 1120 on the tray 1102 by one or more clamp arms 1114 interlocking into grooves on the shaft 1120. In this example, the second tray 1122 on the bottom does not include the shaft 1120 of the first tray 1102 on the top. The clamp arms 1114 may fit into the handle 1110 to subsequently fit into the shaft 1120. To couple with the shaft 1120, the handle 1110 can include a hinge axle 1112 and a compression spring 1116 in between the clamp arms 1114. The hinge axle 1112 and spring 1116 enable the clamp arms to be pinched together to release and uncouple the clamp arms tips 1118 from grooves in the shaft 1120. The clamp arms 1114 can pivot about the hinge axle 1112. Otherwise, as shown in FIG. 11(B), when the clamp arms 1114 are not pinched together, the clamp arm tips 1118 are interlocked with the shaft 1120 connected to the first tray 1102. This is because the compression spring 1116 above the hinge axle 1112 forces the clamp arm tips 1118 toward each other. While placing the handle 1110 onto the main shaft 1120, the clamp arm tips 1118 slide over the shaft 1120 which results in the opening of the clamp system and causes the compression spring 1116 to compress further more. The clamp system of the handle 1110 remains open until it reaches the groove on the main shaft 1120, where the spring 1116 suddenly expands, causing the clamp tips 1118 to move inward and hit the shaft 1120 body, snapping the handle 1110 onto the shaft 1120 of the first tray 1102. To remove the handle 1110, the ends of the clamp arms 1114 can be pinched or pushed together at the grip portion so that the clamp arm tips 1118 open and the handle 1110 is released from the grooves on the shaft 1120. The first tray 1102 on top and the second tray 1122 on the bottom are also configured to interlock with each other to seal the two trays together. The trays can also be separated for easy cleaning and removal of the applicator tools.

Figure 12:
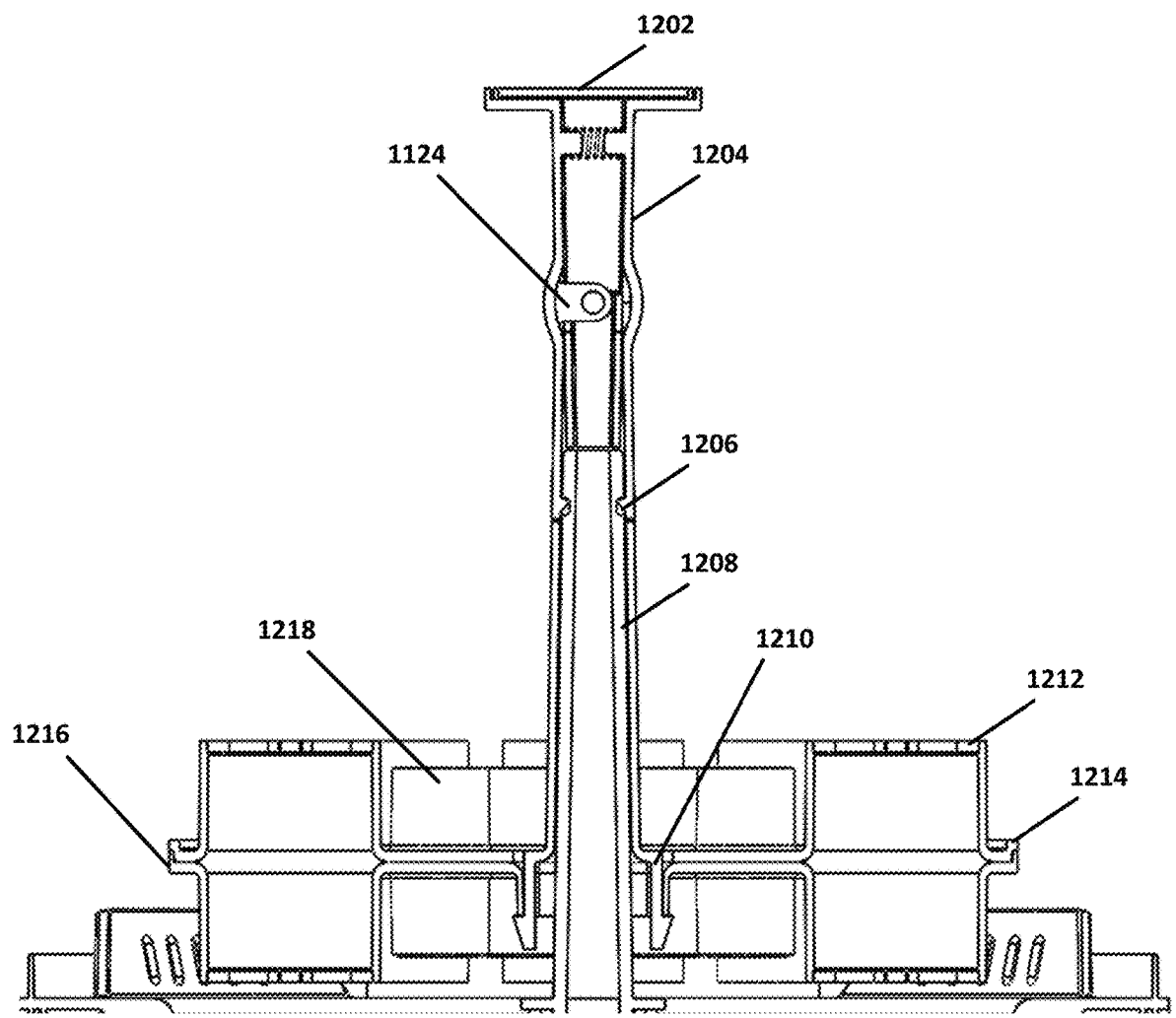
FIG. 12 illustrates a cross-section view of the fourth tool holder component in accordance with one embodiment.

FIG. 12 illustrates a cross-section view of the example applicator tool holder of the fourth example of the cleaning device in accordance to various embodiments. In this example and as described in FIGS. 10-11, an applicator tool holder includes a top tray 1214 with a number of overmolded cups 1212 of various sizes to accommodate different types of applicator tools, such as the smaller overmolded cup 1218. The bottom tray 1216 has overmolded cups that mirror the top tray 1214. The bottom tray 1216, however, does not have a shaft, but is configured with an interlocking mechanism 1210 to lock with the shaft 1208 of the top tray 1214. To enable a user to move and transport the applicator tool holder without touching the applicator tools, the applicator tool holder can have a handle 1202 with a grip top portion to a user to hold onto. The handle 1202 may be coupled to a shaft 1208 on the top tray 1214. To couple the handle 1202 to the shaft 1208, one or more clamp arms 1204 can, via a hinge axle and spring configuration 1124, interlock into grooves 1206 on the shaft 1208. Depending on whether the status of the cleaning device is performing a cleaning process or a drying process, the applicator tool holder may be moved vertically up or down to a lower position or an upper position.

Figure 13:
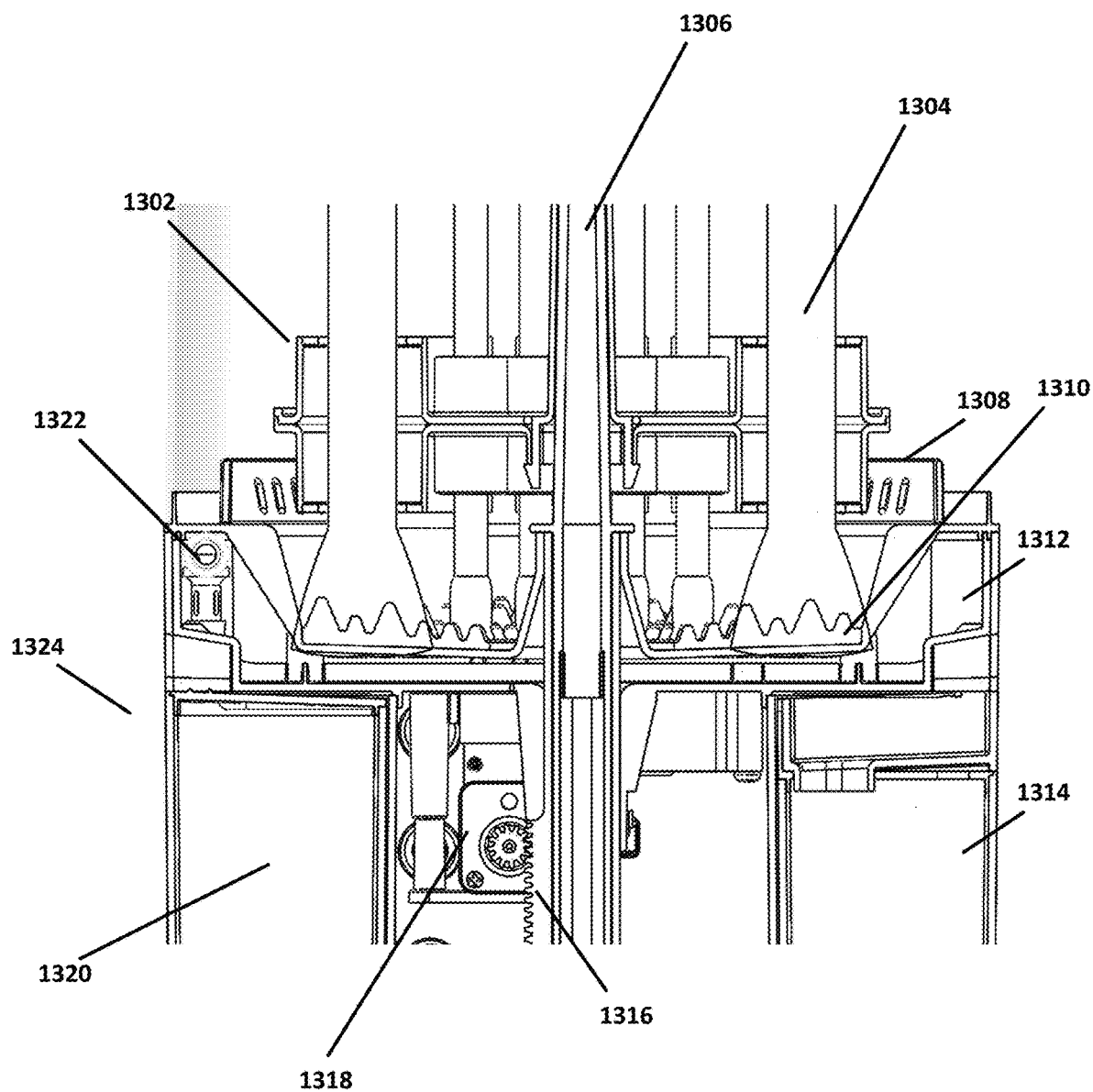
FIG. 13 illustrates a cross-section view of the fourth example cleaning device in accordance with one embodiment.

FIG. 13 illustrates a cross-section view of the fourth example cleaning device in accordance to various embodiments. In this example, the applicator tool holder 1302 is in a lower position such that brushes 1304, shown in this example, are in contact with a textured mat 1310 within a washing bowl 1312 of cleaning chamber 1324. During a cleaning cycle or process, the applicator tool holder 1302 can be lowered into the washing bowl 1312 by motor 1318 driving drive mechanism 1316 to move the applicator tool holder vertically using column 1306 attached to the shaft of the applicator tool holder 1302. When the applicator tool holder 1302 is lowered into washing bowl 1312, the bristled ends of brushes 1304 are in contact with mat 1310. The mat 1310 is shaped with a plurality of protrusions of various sizes. The cleaning chamber 1324, in this example, also includes a liquid dispensing tank 1320, which can store liquid, for example cleaning liquid such as detergent, or a rinsing liquid such as water. The liquid may be dispensed from dispenser 1322 into the washing bowl 1312 to saturate the bristled ends of the brushes 1304. The waste liquid from the cleaning may be drained into drain tank 1314, which may be removed to dispose of the waste liquid. After the cleaning cycle, a drying cycle or process may be initiated. Although not shown in FIG. 13, the drying cycle can include the applicator tool holder 1302 being lifted to an upper position via the motor 1318 and drive mechanism 1316, such that the bristled ends of the brushes 1304 are aligned with air vents 1308. The air vents 1308 direct air from fans (not shown) within the cleaning chamber 1324.

Figure 14:
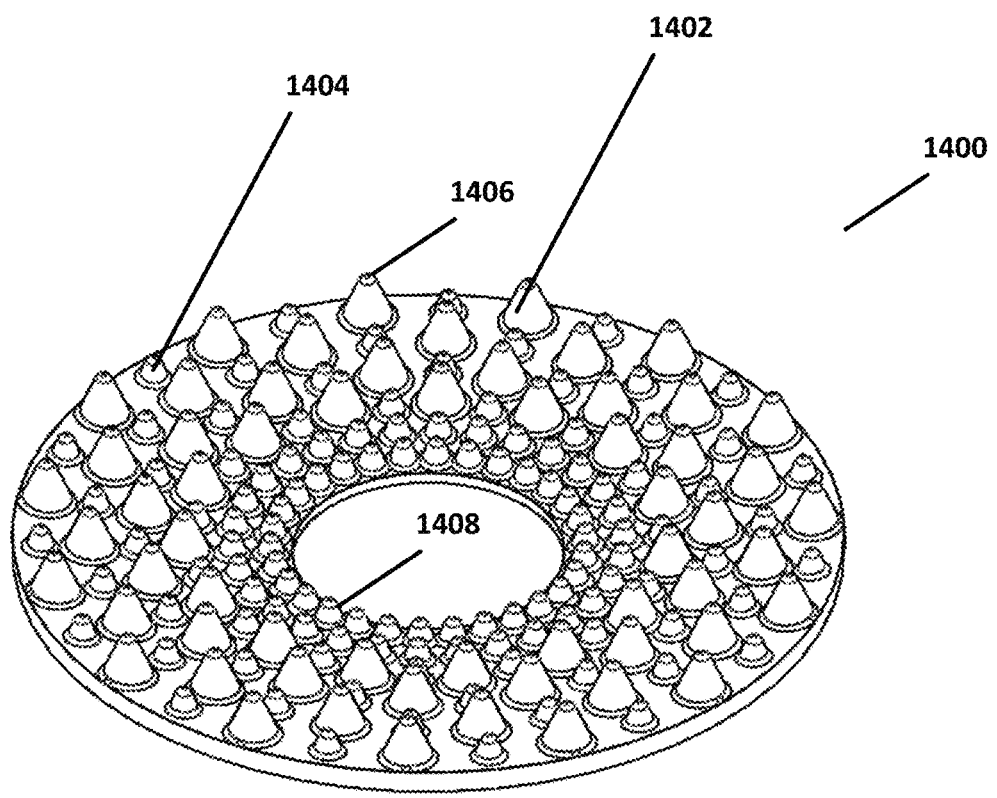
FIG. 14 illustrates a perspective view of a fourth drying component in accordance with one embodiment.

FIG. 14 illustrates a perspective view of an example mat 1400 utilized in accordance to various embodiments. In this example, the mat 1400 is constructed with various cones or protrusions from a surface of the mat. The mat 1400 may have large cones 1402 on a surface of the mat to be contacted with the application portions or applicator heads of the applicator tools during the cleaning cycle. There may also be smaller cones 1404 interspersed with the large cones 1402. In this example, an outer section of mat 1400 may have a combination of large cones 1402 and small cones 1404 dispersed with a lower density for larger applicator tools arranged on the applicator tool holder. The inner section 1408 may be arranged with the small cones 1404 with a higher density for smaller applicator tools. In one example, the large cones 1402 can be constructed with a base diameter of 8 mm, a height of 8 mm, and a top diameter 1406 of 2.5 mm. The small cones 1404 can be constructed with a base diameter of 4.5 mm, a height of 4 mm, and a top diameter of 2.5 mm. However, it is understood that various sizes and dimensions of the cones or other shapes may be utilized according to embodiments described herein.

Figure 15:
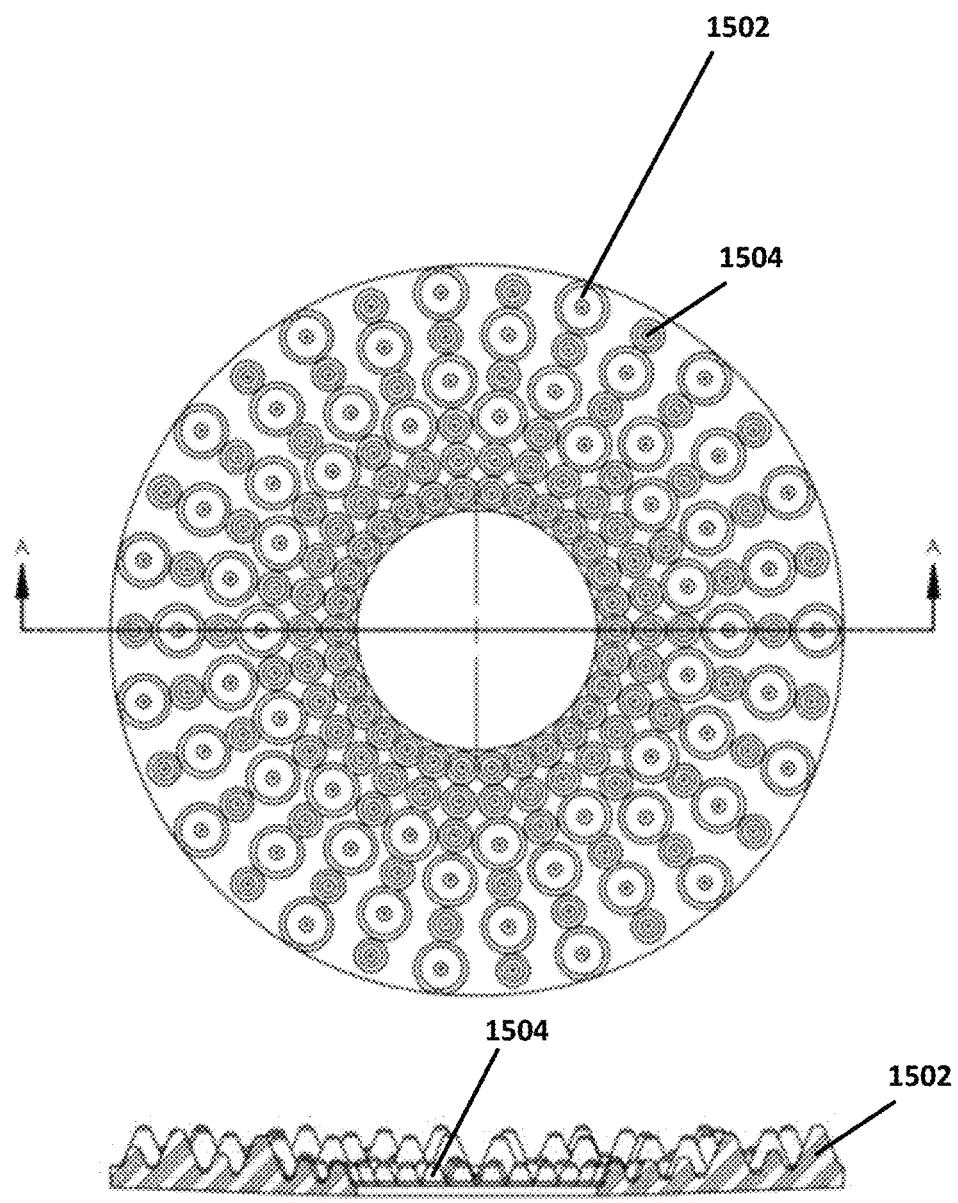
FIG. 15 illustrates a top view and a cross-section view of the fourth drying component in accordance with one embodiment.

FIG. 15 illustrates a top view and a cross-section view of the example mat utilized in accordance to various embodiments. As shown in in FIG. 15, the mat may have large cones 1502 on a surface of the mat to be contacted with the application portion of the applicator tools during the cleaning cycle. There may also be smaller cones 1504 interspersed with the large cones 1502 in the outer section of the mat suitable for cleaning larger applicator tools and arranged radially from the center. The inner section of the mat closer to the center may be arranged with the small cones 104 with a higher density for smaller applicator tools.

Figure 16:
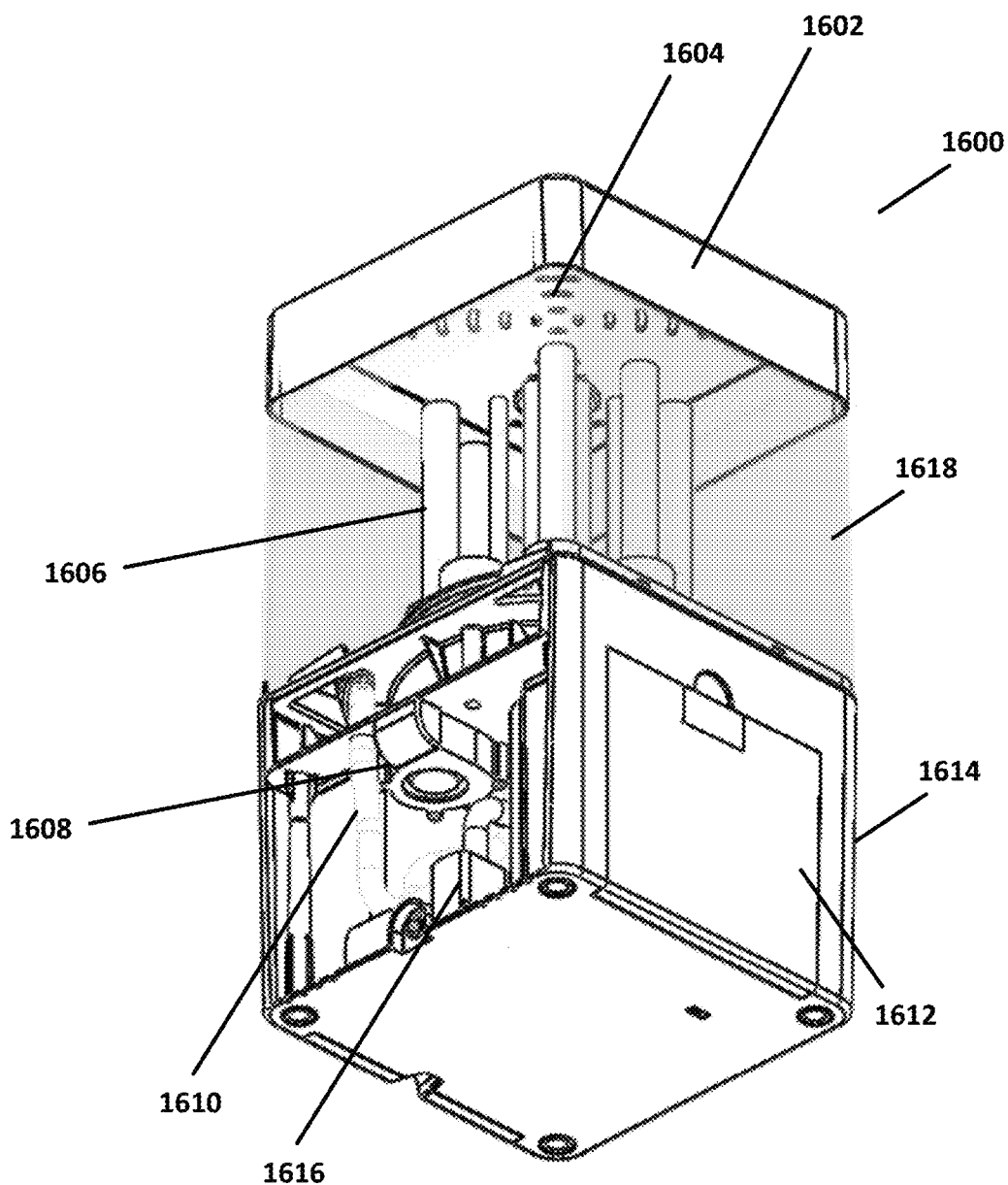
FIG. 16 illustrates a perspective view of the fourth example cleaning device in accordance with one embodiment.

FIG. 16 illustrates a perspective view of the fourth example cleaning device 1600 in accordance to various embodiments. In this example, the cleaning device 1600 has a lid 1602 to fit on top of the applicator tool holder holding brushes 1606, or other applicator tools or instruments. The lid 1602 may be perforated with vents 1604 to allow for flow of air out of the cleaning device 1600. The lid 1602 may be configured to connect and seal to a middle portion drying chamber 1618, attached to the cleaning chamber 1614. The middle portion 1618 may be clear or translucent for visibility on whether a cleaning cycle or drying cycle is being performed on the brushes 1606. The middle portion 1618 also serves as a drying chamber for when the brushes 1606 are in an upper position such that the bristled end of the brushes are aligned with air vents at the edge of the washing bowl of the cleaning chamber 1614. [[Although cosmetic brushes are used in this example, other applicator tools can be cleaned in the example cleaning device, such as paint brushes, sponge-tipped tools, etc.]] The cleaning chamber 1614, in this example, is opened to expose some of the inner workings according to various embodiments. For example, the cleaning chamber 1614 can house a liquid dispersing tank (not shown) with an inlet 1610 to dispense liquid in a washing bowl of the cleaning chamber 1614 to saturate the bristled ends of the brushes 1606. The cleaning chamber 1614 can also house a fan, blower, other drying mechanism 1608 to blow air into the drying chamber 1618 to dry the bristled ends after the cleaning cycle is complete. A motor 1616 can drive the column that couples with a shaft of the applicator tool holder to move the applicator tool holder vertically depending on the cycle or process being performed (e.g., cleaning or drying) on the brushes 1606. After cleaning, the liquid may be drained from the bowl in a drain tank 1612, which can be easily removed from the cleaning chamber 1614 for easy disposal of the waste liquid. Additionally, vents or openings 1604 may be located on the top portion 1602 or on the cleaning chamber 1614.

Figure 17:
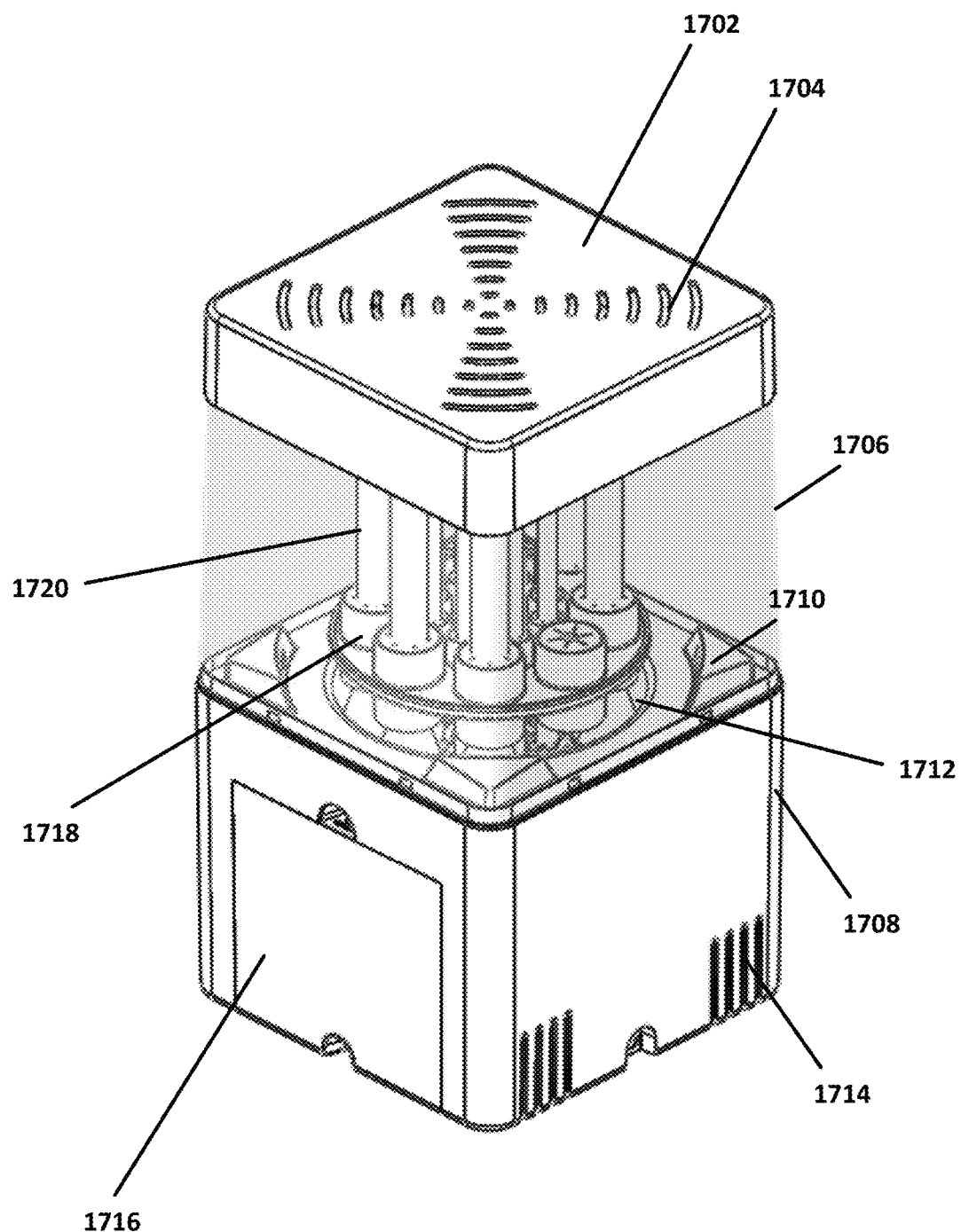
FIG. 17 illustrates a perspective view of the fourth example cleaning device in accordance with one embodiment.

FIG. 17 illustrates another perspective view of the fourth example cleaning device of FIG. 16 in accordance to various embodiments. As described above, the lid 1702 may be constructed with openings, perforations, or vents 1702 to allow for air circulation. The lid 1702 can be fitted to seal with a middle portion drying chamber 1706 attached to the cleaning chamber 1708. Blowing mechanisms are installed within the cleaning chamber 1708. In this example, four outlet vents 1710 are integrated at an upper edge of the wash bowl 1712. The outlet vents 1710 direct air from the blowing mechanisms to the bristled ends of brushes 1720 to dry them in the drying chamber 1706 when the brushes are in the upper position. The brushes 1720 are held in applicator tool holder 1718, which is configured to be attachable to the lid 1704. During a cleaning cycle, liquid may be dispensed into the wash bowl 1712 to saturate the bristled ends of the brushes. In some embodiments, the applicator tool holder 1718 may be rotated or the wash bowl 1712 may be oscillated to aid in cleaning the applicator tools. For example, the movement of the applicator tool holder 1718 and/or the wash bowl 1712 can ensure thorough dislodging of materials collected on the bristles, sufficiently lathering of any cleaning liquid in the wash bowl, and/or sufficiently rinsing of any remaining cleaning liquid residue in the bristles with water or other rinse liquid. After the cleaning cycle is completed, the applicator tool holder 1718 along with the brushes 1720 is moved up in a vertical direction, for example about 40 mm (1.5 in), into the drying chamber 1706 so that the brush heads are aligned with the air outlet vents 1710. The blowing mechanisms at the upper edge of the cleaning chamber 1706 are turned on to blow drying air into the drying chamber 1706. The applicator tool holder 1718 or the individual brushes 1720 may start rotating simultaneously to allow more air flow through the brush heads. There are openings 1704 on the top lid/cover to allow air out. Additionally, in this example, there are vents 1714 at the back and bottom of the cleaning chamber 1708 so that the air can flow in (intake) for the blowing mechanisms to blow air into the drying chamber 1706. Other vents may be located in the cleaning chamber 1706 to cool the motor or the fan.

Figure 18:
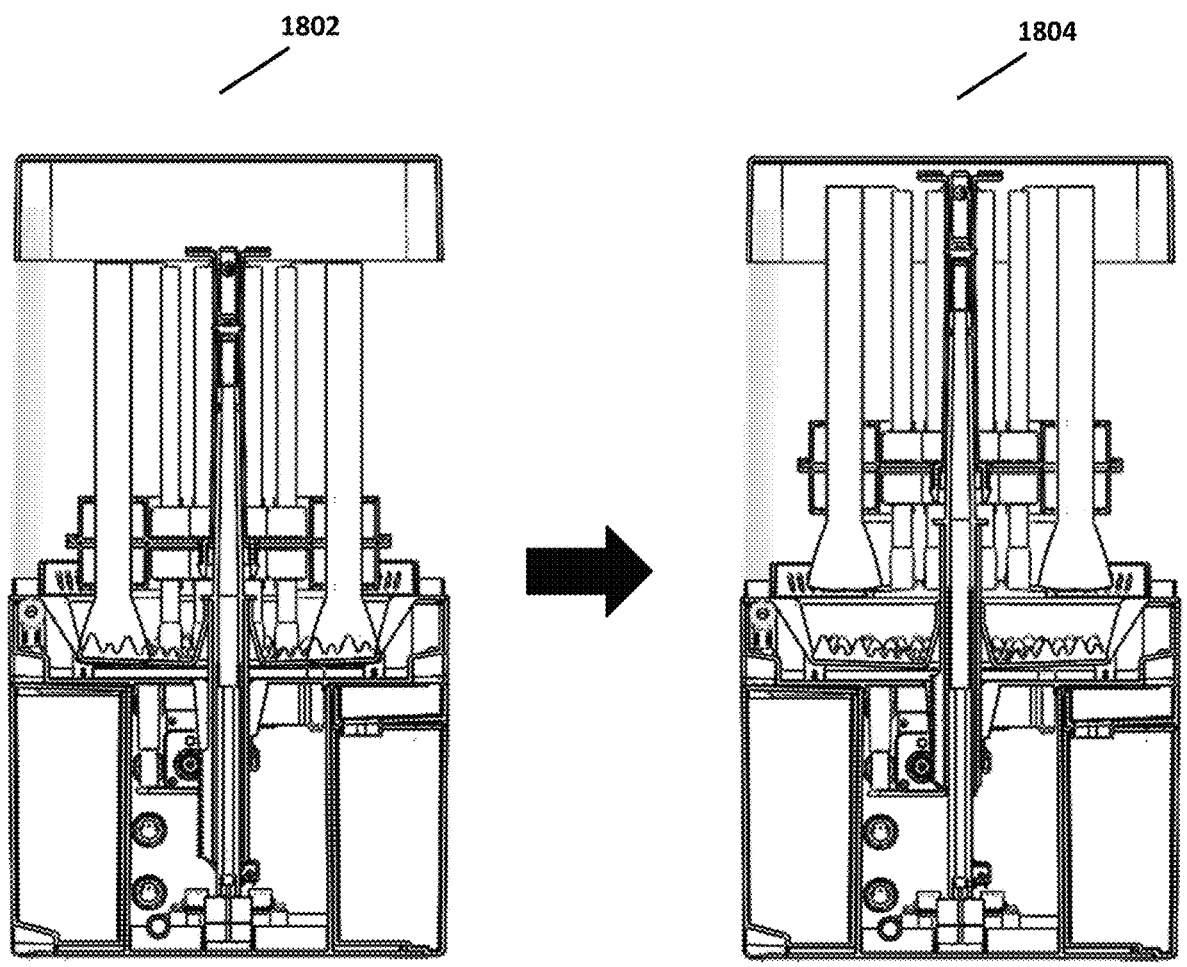
FIG. 18 illustrates cross-section views of the fourth example cleaning device in accordance with one embodiment.

FIG. 18 illustrates a cross-section view of the fourth example cleaning device utilized in accordance to various embodiments. Here, the cleaning device in a cleaning cycle with the applicator tool holder in a lower position is shown in 1802. The cleaning device in a drying cycle with the applicator tool holder in an upper position is shown in 1804. To initiate a cleaning cycle, a user may place several brushes into the applicator tool holder. The applicator tool holder of the cleaning device can hold the applicator tools when the wands of the applicator tools are inserted into the applicator tool holding receptacles formed by the overmolded cups of the coupled top and bottom trays. The cleaning cycle may then be initiated by, among other things, the user pressing a button, lowering the applicator tool holder, or closing the lid to automatically start the cleaning cycle. During a cleaning cycle, the applicator tool holder may be lowered into a lower position. For example, the lower position is when the bristled ends of the brushes inserted into the applicator tool cleaning device are in the wash bowl and in contact with a textured mat at the bottom of the wash bowl. The mat can be textured with protrusions on the surface of the mat contacting the bristles. The mat can be divided into different radial sections with different sizes of protrusions depending on the brushes held in those sections. In some embodiments, a cleaning liquid can be dispensed into the wash bowl. Further, the applicator tool tray of the holder, the wash bowl, or mat may be rotated to further contact the bristles against the protrusions on the mat to help dislodge collected materials on the bristles, lather the cleaning liquid, or rinse residual cleaning liquid within the bristles of the brushes. The cleaning cycle may be timed, for example, the brushes may be saturated in cleaning liquid for a specific amount of time. After the cleaning liquid has been distributed to saturate the brushes in the wash bowl, the cleaning liquid can be drained from the wash bowl into a waste liquid tank for disposal. A rinsing liquid may then be dispensed into the wash bowl to rinse the brushes with a similar rotating technique for the applicator tool holder or wash bowl. Once the rinse is complete, the rinsing liquid can be drained into the waste liquid tank.

After the cleaning cycle is completed, the device may indicate to the user through an interface or a light that the cleaning cycle is complete. In some embodiments, a drying cycle is automatically initiated after the cleaning cycle is complete. Alternatively, the device may wait for a manual input from the user to initiate the drying cycle. During a drying cycle, the applicator tool holder is lifted vertically to move the bristled ends of the brushes out of the wash bowl into an upper position such that the bristled ends are in alignment with fan outlets to blow air into a drying chamber. A drying mechanism blows air through the fan outlets directed at the bristled ends of the brushes to dry them. Although brushes are described in this example, other applicator tools can be cleaned and dried in the same manner such that the drying mechanisms are directed to application portions or applicator heads of suitable applicator tools inserted in the cleaning device. In some embodiments, the drying or cleaning chamber includes, among other things, sensors to determine whether the applicator tools are sufficiently dry, for example by measuring a moisture level or a temperature. Alternatively, the drying cycle may be timed to a set period of time. After the drying cycle is complete, the device may indicate to the user that the applicator tools are dry, for example by a colored light, a blinking light, a display, or a sound. In other embodiments, the applicator tools may be exposed to a UV light or LED light to disinfect or dry the applicator tools.

Various modes of operation can be utilized. In one embodiment, two wash cycles of similar length (i.e., between ten minutes and fifteen minutes each) are used, with the same or different liquid used for each cycle. It should be understood that different speeds and strengths of cycles can be used, and that the cycles can have different lengths. In some embodiments one cycle uses a cleaning solution while one cycle might use water to wash away the cleaning solution. After the last washing cycle, a drying cycle can commence in at least some embodiments that dries the applicator tools, such as cosmetic brushes, or other instruments. This can be anywhere from ten minutes to twenty minutes or longer in some embodiments, depending upon factors such as the type of drying mechanism used and the type of applicator tool being cleaned. In some embodiments a moisture sensor or other mechanism can be used to end the drying cycle after the applicator tools are sufficiently dry, such as by having a maximum amount or level of moisture in the tank. In some embodiments a user presses an activate button once, which causes the device to automatically run through all the cycles. In other embodiments a user must manually activate each cycle, and may also have to end each cycle in some embodiments. Some devices enable a user to program the number of cycles, cycle length, and other information. In some embodiments a device can determine the number or type of applicator tools to be cleaned and adjust the cycle parameters appropriately.

There can also be variations of such a cleaning device, such as a personal device that cleans up to ten brushes and requires manual water solution management and an industrial version that may clean and dry dozens of applicator tools and includes, among other things, water inlet and outlet functionality. The industrial version (or some consumer versions) may also include, among other things, an interface to provide more control, such as to set specific times, temperatures (or lack of heat), types of oscillations, and the like. Some designs can include, among other things, a knob, switch, or other input mechanism for selecting among various time, cycle, and/or temperature settings. The drying mechanism might also have various types of air force and heat cycle settings. In some embodiments a user might set a switch or input for a certain type of applicator tool, and the time, cycle, heat, and other settings will be automatically adjusted as appropriate. Certain embodiments may interface with an application, such as may execute on a user's computer or smart phone, in order to enable the user to specify the settings through the app, as well as to enable the user to start the cleaning process or drying process from a remote location. The sizes, materials, and power sources used for each may differ as well. For example, a consumer version might be small and lightweight with rechargeable batteries for portability and ease of use, and may even be retractable for easy storage. A consumer version may also have functionality that enables the device to function as an applicator tool holder or organizer when not in use. An industrial version might be built for durability and include, among other things, a conventional power cord, larger motor, stronger heating element, and other components. Other components can be included as well, such as an ultraviolet or ultrasonic source to aid in material removable and applicator tool/solution purification (such as by killing bacteria and germs), among other such advantages.

The specification and drawings are to be regarded in an illustrative rather than a restrictive sense. It will, however, be evident that various modifications and changes may be made thereunto without departing from the broader spirit and scope of the invention as set forth in the claims.

What is claimed is:

1. A method of cleaning and drying applicator tools comprising:
   receiving, at an applicator tool cleaning device, at least one applicator tool in a tray, the at least one applicator tool having an application portion and a handle, wherein the tray is configured to store the at least one applicator tool by the handle with the application portion facing down;
   receiving, by a processor of the applicator tool cleaning device, a first signal to initiate a cleaning process on the at least one applicator tool;
   lowering the tray into a bowl with a mat arranged at a bottom of the bowl, the mat having protrusions configured to be contacted with the application portion of the at least one applicator tool;
   dispensing cleaning liquid into the bowl;
   oscillating, by a motor of the applicator tool cleaning device, the tray to contact the application portion with the protrusions of the mat;
   removing the cleaning liquid from the bowl;
   dispensing a rinsing liquid into the bowl;
   removing the rinsing liquid from the bowl;
   displaying a first indication that the cleaning process is complete;
   lifting the tray vertically out of the bowl to remove the application portion out of the bowl and align the application portion with an outlet of a drying mechanism of the applicator tool cleaning device that blows air and is vertically above a top of the bowl;
   receiving, by the processor, a second signal to initiate a drying process on the at least one applicator tool;
   blowing air, by the drying mechanism, to the application portion of the at least one applicator tool via the outlet;
   determining, by a sensor of the applicator tool cleaning device, that the drying process is complete; and
   displaying a second indication that the drying process is complete.

2. The method of claim 1, wherein the sensor determines when the drying process is complete based at least in part on a drying time, a temperature within the applicator tool cleaning device, or a moisture level.

3. The method of claim 2, further comprising illuminating an LED or UV light during the drying process.

4. The method of claim 1, the protrusions comprising:
   a plurality of first cones protruding from a surface of the mat configured to be in contact with the application portion; and
   a plurality of second cones protruding from the surface of the mat configured to be in contact with the application portion, the plurality of second cones having different dimensions from the plurality of first cones.

5. The method of claim 4 further comprising a drying mat is divided into two radial areas, a first radial area comprising a combination of the plurality of the first cones and the plurality of the second cones at a first density, and the second radial area comprising the plurality of the second cones at a second density.

6. The method of claim 1 further comprising placing a top portion onto the applicator tool cleaning device to create a water-tight seal between the top portion and the applicator tool cleaning device.

7. The method of claim 1, wherein blowing air further comprises one of blowing hot air and blowing cool air.

8. The method of claim 7, wherein blowing air further comprises using one of a hot air dryer, a cool air dryer and a fan.

* * * * *